United States Patent [19]

Zimmermann et al.

[11] Patent Number: 5,457,200
[45] Date of Patent: Oct. 10, 1995

[54] 3-AMINOPYRAZOLO HETEROCYCLIC DERIVATIVES, AND USE FOR COLORIMETRIC DETERMINATIONS

[75] Inventors: Gerd Zimmermann, Mannheim; Joachim Siedel, Bernried; Günter Frey, Ellerstadt, all of Germany

[73] Assignee: Boehringer Mannheim, Mannheim, Germany

[21] Appl. No.: 67,229

[22] Filed: May 25, 1993

Related U.S. Application Data

[62] Division of Ser. No. 631,797, Dec. 21, 1990, Pat. No. 5,234,818.

[30] Foreign Application Priority Data

Dec. 21, 1989 [DE] Germany ............... 39 42 357.3

[51] Int. Cl.⁶ ............... C07D 487/00; C07D 249/08; C07D 473/00; C07D 231/00
[52] U.S. Cl. ............... 544/281; 544/254; 544/263; 544/236; 546/121; 548/262.4; 548/154; 548/303.1; 548/360.5; 435/28
[58] Field of Search ............... 544/281, 254, 544/263, 236; 546/121; 548/121, 154, 262.4, 303.1, 360.5; 514/212, 258; 435/28

[56] References Cited

U.S. PATENT DOCUMENTS

| 4,918,074 | 4/1990 | Tsuda et al. ............... 514/258 |
| 5,102,869 | 4/1992 | Shiokawa et al. ............... 514/212 |

FOREIGN PATENT DOCUMENTS

| 8602467 | 4/1986 | European Pat. Off. . |
| 0178789 | 4/1986 | European Pat. Off. . |
| 0264192 | 4/1988 | European Pat. Off. . |
| 0268167 | 5/1988 | European Pat. Off. . |
| 423174 | 2/1967 | Japan . |
| 50-90769 | 3/1975 | Japan . |
| 6010493 | 2/1976 | Japan . |
| 0172982 | 9/1985 | Japan . |
| 63-74055 | 4/1988 | Japan . |
| 2051054 | 1/1981 | United Kingdom . |

OTHER PUBLICATIONS

Helvetica Chimica Acta 58, 761 (1975), Vogel and Troxler.
Takamizawa et al, *Chemical Abstracts*, vol. 58, Ref. No. 10214a, 1963 (JA 2347 (62), May 21, 1959).
Kirkpatrick et al, *Journal of Medical Chemistry*, vol. 20, No. 3, pp. 386–393, 1977.
Dziomko et al, *Chemical Abstracts*, vol. 89, p. 627, Ref. No. 433405, 1978.

Primary Examiner—Michael G. Wityshyn
Assistant Examiner—Abdel A. Mohamed
Attorney, Agent, or Firm—Felfe & Lynch

[57] ABSTRACT

The present invention is concerned with the use of certain 3-aminopyrazolo-heterocyclic compounds for the colorimetric determination of hydrogen peroxide, hydrogen peroxide-forming systems, peroxidase, peroxidate-active substances and electron-rich aromatic compounds. The present invention is also concerned with corresponding processes of determination and with agents appropriate therefor. Furthermore, the present invention is concerned with new 3-aminopyrazolo-heterocyclic compounds.

4 Claims, No Drawings ive application of application Ser. No.
3-AMINOPYRAZOLO HETEROCYCLIC DERIVATIVES, AND USE FOR COLORIMETRIC DETERMINATIONS This is a divisional application of application Ser. No. 631,797, filed Dec. 21, 1990, now U.S. Pat. No. 5,234,818.

The present invention is concerned with the use of 3-aminopyrazolo-heterocyclic compounds for the colorimetric determination of hydrogen peroxide, hydrogen peroxide-forming systems, peroxidase, peroxidate-active substances and of electron-rich aromatic compounds, as well as with new 3-aminopyrazolo-heterocyclic compounds and a process for the preparation thereof.

Furthermore, the present invention is concerned with a process for the colorimetric determination of hydrogen peroxide, hydrogen peroxide-forming systems, peroxidase and peroxidate-active substances by means of oxidative coupling of an electron-rich aromatic compound with a heterocyclic compound.

In addition, the present invention is also concerned with an agent for the colorimetric determination of hydrogen peroxide, hydrogen peroxide-forming systems, peroxidase and peroxidate-active substances by oxidative coupling, containing an electron-rich aromatic compound and a heterocyclic compound.

The present invention is also concerned with the use of a 3-aminopyrazolo derivative for the production of an agent for the colorimetric determination of hydrogen peroxide, hydrogen peroxide-forming systems, peroxidase and peroxidate-active substances by oxidative coupling.

The present invention is also concerned with a process for the colorimetric determination of an electron-rich aromatic compound by the oxidative coupling thereof with a heterocyclic compound in the presence of an oxidation agent.

In addition, the present invention is also concerned with an agent for the colorimetric determination of an electron-rich aromatic compound by oxidation coupling, containing a heterocyclic compound and an oxidation agent.

Finally, the present invention is concerned with the use of a 3-aminopyrazolo derivative for the production of an agent for the colorimetric determination of an electron-rich aromatic compound by oxidative coupling.

Not only for analytical chemistry but also for medical diagnosis, the detection of hydrogen peroxide by means of chromogenic substances, with the catalysis of peroxidase or of peroxidate-active substances, for example haemoglogin, is of very great importance. This applies in particular to numerous detection processes in which hydrogen peroxide is formed as intermediate and subsequently, in the presence of appropriate chromogenic compounds, preponderantly in the presence of a peroxidase (POD), as catalyst, is converted into a compound which can be detected optically and is in a quantitative relationship to the hydrogen peroxide formed. Furthermore, peroxidase is frequently used as an enzyme label in immune tests and is detected by the addition of hydrogen peroxide and the above-mentioned chromogenic substances.

As examples, the following compounds are mentioned which, with the oxidases indicated in brackets, represent hydrogen peroxide-forming systems: glucose (glucose oxidase), galactose (galactose oxidase), L-amino acids (L-amino acid oxidase), cholesterol (cholesterol oxidase), uric acid (uricase), sarcosine (sarcosine oxidase) and glycerol (glycerol oxidase).

Numerous chromogens and indicator systems have already been described and used for the detection of hydrogen peroxide/peroxidase. One of the best known ones is that of Trinder (see Ann. Clin. Biochem., 6, 24–27/1969), an indicator system in which phenol is oxidatively coupled with 4-aminoantipyrine in the presence of peroxidase with the action of hydrogen peroxide to give a coloured material. As coupling component, instead of phenol there can also be used phenol derivatives, aniline derivatives, naphthol, naphthol derivatives, naphthylamine, naphthylamine derivatives and other compounds which react in a similar manner. 4-Aminoantipyrine as coupling component can be substituted, for example, by aminoantipyrine derivatives, vanilindiaminesulphonic acid, methylbenzthiazolinone hydrazone (MBTH), sulphonated methylbenzthiazolinone hydrazone (SMBTH) and similar systems described by S. Hünig (cf. "The Chemistry of Synthetic Dyes", K. Venkataraman ed., Vol. IV, pp. 189–193, publ. Academic Press, New York, San Francisco, London, 1971).

In published European Patent Specification No. A-0,033, 539, for the achievement of a better colour stability of the coloured material resulting in the case of the oxidative coupling of 4-aminoantipyrine with phenols, there is suggested the replacement of 4-aminoantipyrine by 4-aminoantipyrine derivatives which bear a doubly substituted phenyl radical. The coloured materials which can thus be obtained display $\lambda_{max}$ values in the range of about 500 to 550 nm.

In all, a great disadvantage of the previously described redox indicator systems based upon 4-aminoantipyrine or N-methylbenzthiazolinone-hydrazone is the fact that, by means of oxidative coupling with electron-rich aromatic compounds, for example phenols and anilines, coloured materials result, the $\lambda_{max}$ values of which lie in the region of about 500±50 nm. Oxidative coupling reactions are frequently employed in the case of the analysis of body fluids, for example blood, plasma, serum, urine, saliva and the like. However, especially in the case of haemolysed plasma and sera, i.e. haemoglobin-containing plasma and sera, problems arise in the case of the use of redox indicator systems of the prior art which enter into oxidative coupling reactions which are conditioned by the relatively high inherent absorption of such sample materials in the region of about 500 nm. Impairments of the measurement are then the more serious the smaller is the concentration of the serum component to be determined.

Furthermore, because of the blank value instability caused by autoxidation or of the instability of the colour produced at the pH values of about 6 to 8 needed for the enzymatic reaction, many of the known redox indicators are not suitable for the development of a hydrogen peroxide determination.

This applies particularly to 2-hydroxy-3-amino-5,7-dimethylpyrazolopyrimidine described, inter alia, by W. Ried and E.-V. Möcher in Liebigs Ann. Chem. 647, 116–144/1961 and in Liebigs Ann. Chem. 647,144–154/1961 which is so unstable towards oxygen that it was not possible to obtain it as a pure compound.

In spite of the large number of known redox indicators for the detection of hydrogen peroxide, peroxidase and peroxidate-active substance, the search is still being made for those compounds which can be used in as many test systems as possible, especially for the determination of components of body fluids, which display a high sensitivity over a wide pH range and which are not disturbed by serum components.

Therefore, in the scope of the objects of the present invention, appropriate compounds are to be made available which can be used for the determination of hydrogen peroxide, hydrogen peroxide-forming systems, peroxidase, peroxidate-active substances and of electron-rich aromatic compounds, which, by oxidative coupling with phenols, anilines and other couplers, give coloured materials, the absorption of which is sufficiently long-waved in order not to be disturbed by the inherent absorption of blood plasma or serum, which satisfy the requirements with regard to blank value stability and colour stability at the measurement pH and in the case of which the colour yield in the case of the oxidative coupling is not disturbed by blood components.

Thus, the present invention is concerned with the use of pyrazolo derivatives of the general formula:

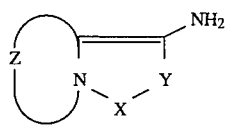
(I)

wherein —X—Y— signifies —NR$^1$—CO— or —N=CR$^2$— in which R$^1$ is an alkyl radical and R$^2$ is alkyl, alkenyl, alkoxy, alkylthio, aryl or aralkyl, optionally substituted in each case by hydroxyl, dialkylphosphinyl, carboxyl, SO$_3$H, PO$_3$H$_2$, a salt of one of these acid residues and/or alkoxycarbonyl; amino, which is optionally substituted by one or two alkyl radicals which, in turn, are optionally substituted by one or more hydroxyl, carboxyl and/or alkoxycarbonyl radicals, when amino is substituted by two alkyl radicals these radicals can also be joined to give a ring which, apart from the nitrogen atom of the amino group, can optionally be interrupted also by oxygen, sulphur or a further nitrogen atom or amino is optionally substituted by one or two acyl radicals, alkoxy- and/or aralkoxycarbonyl radicals, H$_2$N—CO—, alkyl, aralkyl- and/or arylcarbamoyl radicals; or is hydrogen, carboxyl, alkoxycarbonyl, carboxamido or halogen and Z signifies —NR$^3$—N=N—, wherein R$^3$ is an alkyl or aralkyl radical or Z is an unsaturated chain containing 3 to 5 members of nitrogen atoms or carbon atoms and optionally one or more nitrogen or sulphur atoms, whereby carbon atoms are optionally substituted by alkyl, alkoxy, alkylthio, hydroxyl, aralkyl, aryl, carboxyl, carboxamido, alkoxycarbonyl, cyano, amino, which is optionally substituted by one or two alkyl radicals which, in turn, are optionally substituted by one or more hydroxyl, carboxyl and/or alkoxycarbonyl radicals, or halogen and whereby nitrogen atoms which are not connected via a double bond are substituted by alkyl or aralkyl and two heighbouring chain substituents can optionally form an alkylene radical which, in turn, is optionally substituted or anellated with aryl, as well as optionally the corresponding tautomeric forms and the salts thereof for the colorimetric determination of hydrogen peroxide, hydrogen peroxide-forming systems, peroxidase or peroxidate-active substances and electron-rich aromatic compounds.

"Alkyl", also in alkyltio, dialkylphosphinyl, alkylcarbamoyl and aralkyl radicals, hereby means a straight-chained or branched alkyl radicals containing up to 6 and preferably up to 4 carbon atoms, the methyl, ethyl, propyl, isobutyl and tert.-butyl radicals being preferred.

When an amino group is substituted by two alkyl radicals, these radicals can also be joined to form a ring in such a manner that, in all, it represents a ring interrupted by a nitrogen atom. Hereby preferred are those amino groups which, in all, represent a five- or six-membered ring and which, in turn, is optionally interrupted by oxygen, sulphur or nitrogen, the morpholino radical being especially preferred.

"Alkoxy", also in alkoxycarbonyl and aralkoxycarbonyl radicals, stands for a straight-chained or branched alkoxy radical containing up to 6 and preferably up to 4 carbon atoms, the methoxy, ethoxy, propoxy, isobutoxy and tert.-butoxy radicals being preferred.

"Aryl", also in arylcarbamoyl radicals, means a carbon aromatic or heteroaromatic radical, preferably one with 6 to 10 ring atoms and especially a phenyl or naphthyl radical which can additionally also be substituted by alkyl, alkoxy and/or halogen, the phenyl radical being especially preferred.

An "aralkyl radical", also in an aralkylcarbamoyl radical, means a radical in which an alkyl radical defined as hereinbefore is substituted by an aryl radical as hereinbefore defined, the benzyl radical being preferred.

An "aralkoxy" radical, for example an aralkoxycarbonyl radical, designates a radical in which an alkoxy radical as defined hereinbefore is substituted by an aryl radical as hereinbefore defined, the benzyloxy radical being preferred.

"Halogen" stands for fluorine, chlorine, bromine or iodine, fluorine and chlorine being preferred.

An acyl radical signifies the residue of a carboxylic acid which can contain alkyl, aralkyl or aryl radicals, the acetyl, phenylacetyl and benzoyl radicals being preferred.

By an alkylene radical is to be understood a straight-chained or branched, saturated or unsaturated hydrocarbon chain containing 3 to 5 and preferably 3 or 4 carbon atoms with two free bonding positions. Examples therefore include

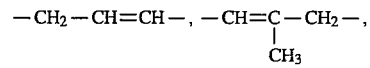

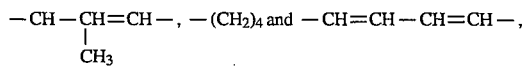

the butadiendiyl radical (—CH=CH—CH=CH—) and the tetramethylene radical (—(CH$_2$)$_4$—) being preferred. An alkenyl radical is a straight chained or branched hydrocarbon chain containing 2 to 5 carbon atoms with at least one double bond. For example the vinyl radical is preferred. As dialkyl phosphine residue is to be understood

whereby alkyl has the meanings given above. The dimethylphosphinyl residue is preferred.

As salts of SO$_3$H, PO$_3$H$_2$ and carboxyl residues, there can be used alkali metal and alkaline earth metal salts and also ammonium salts. By alkali metal salts are to be understood lithium, sodium, potassium, rubidium and caesium salts, whereby lithium sodium and potassium salts and especially sodium and potassium salts are preferred. Alkaline earth metals salts are those of beryllium, magnesium, calcium, strontium or barium, the magnesium and calcium salts being preferred and the calcium salts being especially preferred. As ammonium salts, there can be used the unsubstituted ammonium ion NH$_4^+$. However, it is also possible to use those ammonium salts in which the ammonium ion is substituted by up to 4 alkyl, aryl or aralkyl radicals. For these radicals, there apply the previously given definitions, whereby as alkyl radicals the methyl, ethyl and n-propyl radicals are preferred, as aryl radical the phenyl radical and as aralkyl radical the benzyl radical are especially preferred.

As carboxamido radical is to be understood the CONH$_2$ radical but also those radicals in which the amino group is substituted by one or two alkyl radicals which optionally contain one or more hydroxyl, carboxyl and/or alkoxycarbonyl radicals.

In the pyrazolo derivatives used according to the present invention of general formula (I), Z is preferably so positioned that at least one double bond of the unsaturated chain stands in conjugation with the double bond or with the nitrogen atom in general formula (I).

For a compound of general formula (I), tautomeric forms can also be possible. These are also to be regarded as being covered by general formula (I).

The 3-aminopyrazolo derivatives of general formula (I) can be used as free amines. Preferably, however, they are used as the corresponding ammonium salts. For this purpose, salts with the most varied acids are possible. Especially preferred are those amines of general formula (I) which are present as salts with a mineral acid, for example hydrochloric acid, sulphuric acid, phosphoric acid or nitric acid. The hydrochlorides of the compounds of general formula (I) have proved to be outstandingly useful.

According to the present invention, preferred compounds are those of the following general formulae (II) to (XIII):

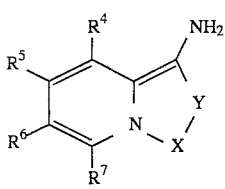 (II)

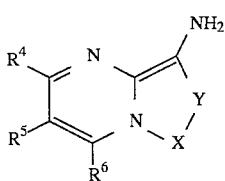 (III)

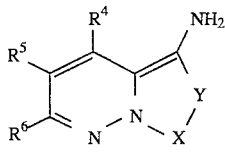 (IV)

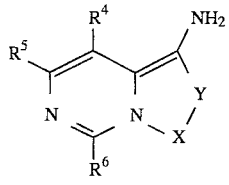 (V)

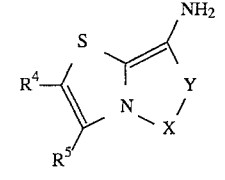 (VI)

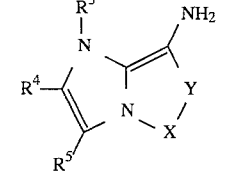 (VII)

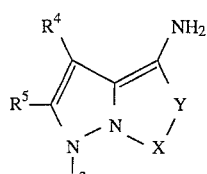 (VIII)

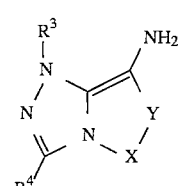 (IX)

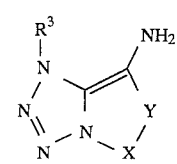 (X)

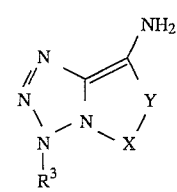 (XI)

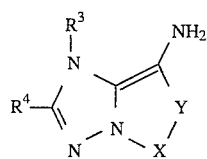 (XII)

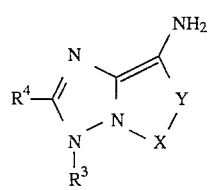 (XIII)

as well as possibly the corresponding tautomeric forms and the salts thereof.

X—Y and $R^3$ hereby have the same meanings as given hereinbefore. $R^4$, $R^5$, $R^6$ and $R^7$, which can be the same or different, stand for hydrogen, hydroxyl, alkyl, alkoxy, alkylthio, aralkyl, aryl, carboxyl, alkoxycarbonyl, carboxamido, cyano, amino, which is optionally substituted by one or two alkyl radicals which, in turn, are optionally substituted by one or more hydroxyl, carboxyl and/or alkoxycarbonyl radicals, or halogen, whereby two neighbouring radicals optionally form an alkylene radical which, in turn, is optionally substituted or anellated with aryl. The definitions of the radicals correspond to those given for the substituents in general formula (I).

Especially preferred for the use according to the present invention are compounds of the general formulae (II), (III), (IV), (VI), (VII) and (IX), optionally the corresponding tautomeric forms and the salts thereof. Quite especially preferred are those compounds in which X—Y has the meaning —N=CR$^2$—, in which R$^2$ can have the meaning given in general formula (I).

The compound 3-amino-2-methylpyrazolo[1, 5-a]pyridine and the salts thereof, especially the hydrochloride, has proved to be especially outstandingly useful for the purpose of the present invention.

Some compounds of general formula (I) are known from the prior art as therapeutically-active compounds. Thus, in published Federal Republic of Germany Patent Specification No. A-22 57 547 and in J. ed. Chem., 17, 645/1974, 3-amino-5,7-dimethylpyrazolo[1,5-a]pyrimidines are described as being 3',5'-cyclo-AMP phosphodiesterase inhibitors. In published Federal Republic of Germany Patent Specification No. A-30 19 019 are described aminopyrazolo [1,5-c]quinazoline derivatives as compounds with pain-killing or analgesic properties which inhibit the secretion of gastric acids and reduce the intestinal activity or display antiperistaltic actions. In published European Patent Specification No. A-0,299,209 are described 3-aminopyrazolopyridines with diuretic, hypotensive, vasodilatory, cardiotonic and the aggregation of blood platelets inhibiting action. Finally, from Chemical Abstracts, 89, 627, 43340r/1978, there is known a tetracyclic 3-aminopyrazolotriazine derivative.

The use of pyrazolo derivatives of general formula (I) as components in oxidative coupling reactions for the colorimetric detection of hydrogen peroxide, hydrogen peroxide-forming systems, peroxidase, peroxidate-active substances or of electron-rich aromatic compounds is not described in the above-mentioned prior art.

For the carrying out according to the present invention of the colorimetric determination of hydrogen peroxide, hydrogen peroxide-forming systems, peroxidase or peroxidate-active substances by means of oxidative coupling, an electron-rich aromatic compound must be reacted with one of the above-described pyrazole derivatives. For better characterisation, in the following, the pyrazolo derivatives according to the present invention are referred to as coupling components and the electron-rich aromatic compounds necessary for the oxidative coupling are referred to as couplers.

As couplers which are able to enter into an oxidative coupling with a coupling component according to the present invention, there can, in principle, be used any compound which can also enter into such a reaction with p-phenylenediamine as coupling component. For an expert, this is easy to test. For this purpose, a series of compounds are known, for example from colour photography. Thus, there can be used the phenolic couplers and couplers with active methylene groups mentioned by T. H. James in "The theory of the photographic process", 3rd ed., pub. Macmillan, New York, 1966, Chapter 17 ("Principles and Chemistry of Color Photography"), pp. 382–396, which enter into an oxidative coupling with the pyrazolo derivatives according to the present invention. The commonest are phenols, phenol derivatives, naphthol, naphthol derivatives, naphthylamine, naphthylamine derivatives and aniline derivatives.

Preferred couplers in the meaning of the present invention are anilinophosphonic acid derivatives such as are described in published European Patent Specification No. 0,175,250, N,N-dimethylaniline, 2,4,6-tribromo-3-hydroxybenzoic acid and N-ethyl-N-3-sulpho-2-hydroxypropyl-m-anisidine.

The detection reaction according to the present invention, which leads to the formation of a coloured material, can, using the example of an N,N-dimethylaniline as coupler, be illustrated as follows:

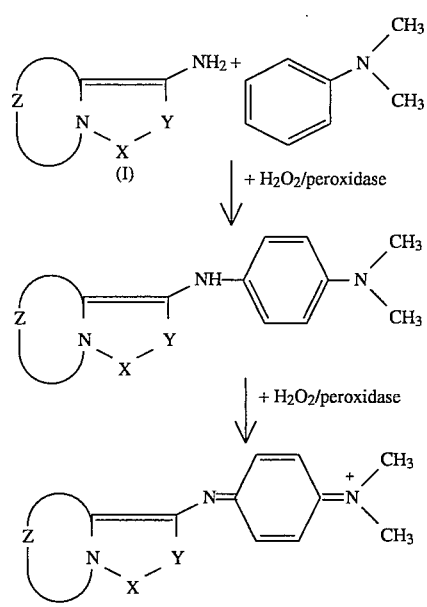

Scheme 1:

Expressed generally, it can be seen herefrom that, for the detection of hydrogen peroxide or of a system producing this, a pyrazolo derivative of general formula (I), a coupler and peroxidase or a peroxidate-active substance must be brought into contact with the sample to be investigated. By hydrogen peroxide-producing systems are to be understood especially the substrate/substrate oxidase pairs which are important in clinical diagnosis of which, by way of example, some of the more important representatives have already been mentioned hereinbefore and in the case of which the substrate is oxidised in the presence of atmospheric oxygen and hydrogen peroxide is produced. Thus, either substrate or substrate oxidase can be detected therewith, depending upon which component is known and, together with the other detection reagents, is to be contected with the sample to be investigated.

If the enzyme peroxidase or a peroxidate-active substance is to be determined, the sample must be reacted with coupler, pyrazolo derivative of general formula (I) and hydrogen peroxide. Alternatively, of course, a substance can also be detected which can act as coupler like, for example, N,N-dimethylaniline in Scheme 1 above. A pyrazolo derivative of general formula (I) and an oxidation agent, which does not necessarily have to be the system hydrogen peroxide/peroxidase but can also be another oxidation agent, for example a peroxide, such as a persulphate or peracetate, or a periodate, chloramine T or especially a cyanoferric complex, for example potassium ferricyanide or an oxidase according to published Federal Republic of Germany Patent Specification No. A-33 31 588, must then be brought into contact with sample.

The colour formed in the case of a positive result can then be used with regard to its intensity as a measure for the amount of the substance to be determined. It can be evaluated visually or photometrically.

With the substances necessary for carrying out the process according to the present invention for the colorimetric determination of hydrogen peroxide, hydrogen peroxide-forming systems, peroxidases, peroxidate-active substances or electron-rich aromatic compounds, there can be produced agents according to the present invention which can be measured in a cuvette. According to the present invention, agents for the determination of hydrogen peroxide, hydrogen peroxide-forming systems, peroxidase or peroxidate-active substances contain an electron-rich aromatic compound and, as heterocyclic compounds which can be oxidatively coupled therewith, a pyrazolo derivative of general formula (I). Separately or together with these compounds, there can be present further materials for the detection of the parameter in question, for example peroxidase for the determination of hydrogen peroxide; peroxidase and enzyme substrate for the determination of the enzyme oxidising the substrate with the formation of hydrogen peroxide; peroxidase and oxidising enzyme for the determination of the enzyme substrate oxidisable by the enzyme with the formation of hydrogen peroxide; or hydrogen peroxide for the determination of peroxidase or peroxidate-active substances. Agents for the colorimetric determination of an electron-rich aromatic compound contain an oxidation agent and a pyrazolo derivative of general formula (I). Further components of the agent according to the present invention can be buffers, as well as possibly wetting agents, activators and other adjuvants.

The reagent components can be pressed into tablets together, separately or, depending on compatibility and expediency, combined with one another as powder or preferably dissolved in water or a buffer solution and optionally subsequently dried or lyophilised to give an agent according to the present invention.

A reagent mixture obtained in this manner is, before use, dissolved in water or some other appropriate solvent and the reagent solution thus prepared. After mixing the sample (for example substrate solution, enzyme solution, serum or plasma) with an aliquot of the reagent mixture, the resultant colour is measured in a photometer and, via the molar extinction coefficient and the added volume or reagent or sample, the concentration or substrate concentration in question then calculated. Kinetic as well as end-point measurements are possible.

Agents according to the present invention can contain the pyrazolo derivatives useable according to the present invention, together with the other substances necessary for the detection of the parameter in question, for example oxidation agents, enzymes, electron-rich aromatic compounds and/or enzyme substrates, buffers, optionally wetting agents and activators, as well as other adjuvants also on or in swellable or absorbent reagent carriers, such as polymer films, papers, membranes, fleece and the like. For this purpose, depending upon compatibility and expediency, one or more solutions can be prepared in the form of aqueous or organic or mixed solutions, depending upon how the reagents or adjuvants dissolve. Absorbent glass or synthetic material fleece are impregnated or sprayed with these solutions. Subsequently, a drying step is carried out. The reagent carriers thus produced can be used either as rapid diagnostic agents for the direct determination of component materials of liquids (for example in body fluids, such as blood, urine or salive, or in foodstuffs, such as fruit juices, milk or the like). The liquid is thereby applied directly on to the reagent carrier or the reagent carrier is briefly dipped into the liquid. A semi-quantitative determination is also possible by associating the resultant colour with a comparison colour. A quantitative evaluation can be carried out by remission photometry. By elution of the above-mentioned reagents with water, buffer or serum from the absorbent carrier, a reagent solution can be prepared with which, as described above, substrates or enzymes can be determined in a cuvette with the use of a photometer. The quantitative determination by remission-photometric evaluation can be carried out especially well when a pyrazolo derivative useable according to the present invention, together with the remaining necessary reagents and adjuvants, and a film-forming synthetic material is worked up to give a reagent film, for example according to Federal Republic of Germany Patent Specification No. C-15 98 153. The smooth surface of such a film thereby gives much less disturbances of the remission and a more homogeneous coloration than the absorbent papers usually employed.

Buffers in the meaning of the present invention have a pH value of 5 to 10 and especially of 6.5 to 8. Phosphate, citrate, borate and GOOD buffers with alkali retal or ammonium counterions are most frequently used but other systems can also be employed.

Wetting agents are especially anionic and cationic ones. Non-ionic wetting agents which activate enzymes can also be employed. Sodium lauryl sulphate, dioctyl sodium sulphosuccinate and alkylaryl polyether alcohols are preferably used.

In the case of the determination of an enzyme or enzyme substrate as an example of a hydrogen peroxide-forming system, as activators there can be used those known for the enzyme reaction in question. The colour-forming reaction is often so quick that an additional activation does not appear to be necessary.

As other adjuvants, it can be helpful to use conventional thickeners, emulsifiers, optical brighteners, contrast agents and the like, such as are known in corresponding tests with other chromogens.

The coupling reaction usually takes place at ambient temperature but can also be carried out without difficulty at a higher temperature, for example at 37° C., if this appears to be desirable for the reaction velocity of, for example, a preceding enzymatic reaction.

For the reactions with enzymes oxidising substrates or with substrates which usually occur, the following concentrations of the test solution have proved to be useful:

| | |
|---|---|
| pyrazolo derivative | 0.05 to 50 mmole/liter, preferably 0.1 to 1 mmole/liter |
| coupler | 0.05 to 100 mmole/liter |
| buffer, pH 5–10, preferably 6.5–8 | 0.05 to 1 mole/liter, preferably 0.1–0.5 mole/liter |
| wetting agent | 0–1.0 mole/liter, preferably 0.05–0.1 mole/liter |
| a) peroxidase | 1.0–5000 KU/liter |
| b) hydrogen peroxide or hydrogen peroxide-producing substrate/ enzyme mixture | 0.1–10 mmole/liter |
| other adjuvants | 0–5 mole/liter. |

The above-given concentration ranges are to be so understood that the lower ranges are, in each case, preferred for photometric tests in cuvettes and the upper ranges for rapid tests or tests on solid carriers.

The pyrazolo derivatives useable according to the present invention display many advantages. Thus, because of the quantitative or almost quantitative reaction with the corresponding couplers, they make possible a very high colour yield. The coloured materials produced by the oxidative coupling and especially those which arise with aniline derivatives according to published European Patent Specification No. A-0,175,250 as couplers are stable and display a high extinction. Furthermore, the absorption maximum ($\lambda_{max}$) of the coloured materials is so high that even haemolysed plasma or serum as sample material can be used. The pyrazolo derivatives useable according to the present invention are also characterised by a rapid colour formation with a coupler under oxidative coupling conditions. Furthermore, the pyrazolo derivatives useable according to the present invention show only a low tendency towards auto-oxidation so that they display the storage stability necessary for commercial tests.

The present invention also provides pyrazolo derivatives which are not known from the prior art and thus are new and which have the general formula:

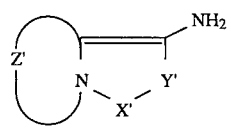  (I')

wherein X'-Y' signifies NR$^{1'}$—CO or N=CR$^{2'}$, whereby R$^{1'}$ is an alkyl radical and R$^{2'}$ is an alkyl, alkenyl, alkoxy, alkylthio, aryl, aralkyl radical optionally substituted by hydroxyl, dialkylphosphinyl, carboxyl, SO$_3$H, PO$_3$H$_2$, a salt of these acid residues and/or alkoxycarbonyl; amino, which is optionally substituted by one or two alkyl radicals which, in turn, are optionally substituted by one or more hydroxyl, carboxyl and/or alkoxycarbonyl radicals, whereby, when amino is substituted by two alkyl radicals, these radicals can be joined to form a ring which, apart from the nitrogen atom of the amino group, can also be interrupted by oxygen, sulphur or a further nitrogen atom or amino is optionally substituted by one or two acyl radicals, alkoxy and/or aralkoxycarbonyl radicals, H$_2$N-CO, alkyl, aralkyl- and/or arylcarbamoyl radicals; or hydrogen, carboxyl alkoxycarbonyl, carboxamido or halogen and Z' signifies NR$^{3'}$—N=N, whereby R$^{3'}$ is an alkyl or aralkyl radical or Z' is an unsaturated chain with 3 to 5 members of nitrogen or of carbon and optionally one or more nitrogen or sulphur atoms, whereby all carbon atoms of the unsaturated chain are parts of a double bond and whereby carbon atoms are optionally substituted by alkyl, alkoxy, alkylthio, hydroxyl, aralkyl, aryl, carboxyl, carboxamido, alkoxycarbonyl, cyano, amino, which is optionally substituted by one or two alkyl radicals which, in turn, are optionally substituted by one or more hydroxyl, carboxyl and/or alkoxycarbonyl radicals, or halogen and whereby nitrogen atoms which are not bound via a double bond are substituted by alkyl or aralkyl or two neighbouring chain substituents optionally form an alkylene radical which, in turn, is optionally substituted or anellated with aryl, as well as the corresponding tautomers and the salts thereof, with the proviso that a) when X'—Y' is N=CR$^{2'}$ with R$^{2'}$ being alkyl or phenyl and Z' is an unsaturated chain of 4 carbon atoms, this is not unsubstituted and is not substituted by alkyl, alkoxy or halogen, b) when Z' is an unsaturated chain of 4 members with 3 carbon atoms and one nitrogen atom on the end of the chain so that in general formula (I') the ring with Z' forms a pyrimidine ring and one or more carbon atoms are substituted by alkyl, alkoxy, alkylthio, hydroxyl, aryl, alkoxycarbonyl or halogen and X'—Y' stands for N=CR$^{2'}$, then R$^{2'}$ does not signify a hydrogen atom, c) when Z' has the meaning:

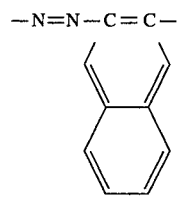

so that in general formula (I') the ring with Z' forms a 1,2,4-triazine ring and X'—Y' stands for N=CR$^{2'}$, then R$^{2'}$ is not a methyl radical:

The meanings of the individual substituents correspond to those given for general formula (I). Furthermore, the statements made for the pyrazolo derivatives useable according to the present invention with regard to advantageous radicals and groups apply in the same way for the new pyrazolo derivatives.

A further subject of the present invention is a process for the preparation of pyrazolo derivatives of general formula (I), wherein a compound of the general formula:

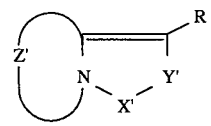  (XIV)

in which X'—Y' and Z' have the same meanings as in general formula (I') and R is a hydrogen atom, is converted a) by reaction with nitric acid or nitric acid in admixture with sulphuric acid and/or acetic anhydride into a compound of general formula (XIV) in which R is a nitro group; or b) by reaction with nitrous acid into a compound of general formula (XIV) in which R is a nitroso group; or c) by reaction with an aromatic diazonium salt into a compound of general formula (XIV) in which R is an arylazo radical, and subsequently reduced.

The synthesis of the compounds of general formula (I') can take place according to known methods by converting a compound of general formula (XIV) by known methods into the corresponding amino compound.

Nitro, nitroso and arylazo radicals, i.e. aryl-N=N radicals in which aryl can have the same meanings as previously given for aryl radicals and other groups containing such radicals, can be converted into amino groups by reduction with reagents such as zinc in an acid, for example hydrochloric acid, or glacial acetic acid sodium dithionite, tin in an acid, for example hydrochloric acid, stannous chloride, or by catalytical hydrogenation, for example in the presence of palladium/carbon. Such reactions are described in Houben-Weyl, Methoden der organischen Chemie, Vol. 11/1, pp. 341 et seq.

The introduction of nitro, nitroso or arylazo groups starting from compounds of general formula (XIV), in which R is a hydrogen atom, can take place by nitration with nitric acid or nitric acid in admixture with concentrated sulphuric acid or acetic anhydride.

By nitrosation with nitrous acid or by azo coupling with aromatic diazonium salts, the nitroso group or an arylazo radical can be introduced. Examples of such reactions are described in Houben-Weyl, Methoden der organischem Chemie, Vol. 10/1 and 10/3.

In some cases, the direct nitrosation of compounds of general formula (XIV) is possible in which R is an alkoxycarbonyl radical, for example an acetyl radical, without first having to carry out a hydrolysis by boiling with concentrated hydrochloric acid to give a compound of general formula (XIV) in which R is a hydrogen atom (cf. Chem. Pharm. Bull., 22, 482/1974).

If heterocyclic compounds of general formula (XIV) are present in which R is a carboxyl, alkoxycarbonyl or alkylcarbonyl radical, then these can be converted into compounds of general formula (XIV), in which R is a hydrogen atom, by hydrolysis with concentrated hydrochloride acid or, in the case of carboxylic acids, by thermal decarboxylation. This is then followed by the introduction of a nitro, nitroso or arylazo radical.

Nitrogen atoms which are not on a double bond and in which radicals X'—Y' and Z' occur with the structure given in general formula (I') must be alkylated or aralkylated. The N-alkylation or N-aralkylation can be carried out by reaction of the appropriate compounds of general formula (XIV), in which R has the above-given meaning, with alkylation or aralkylation agents, for example alkyl or aralkyl halides, dialkyl or diaralkyl sulphates or arylsulphonic acid alkyl or aralkyl esters in the presence of a base, for example sodium hydride, a tertiary amine, an alkali metal carbonate or sodium hydroxide, in a solvent, for example dimethylformamide or an aqueous-alcoholic system.

The starting materials necessary have either been described or can be synthesised analogously to known compounds. Information regarding the preparation of the heterocyclic systems are contained in the following publications: G. P. Ellis, "Synthesis of fused Heterocycles", in "The Chemistry of Heterocyclic Compounds", E. C. Taylor, ed., 1987, pub. John Wiley & Sons; P. N. Preston, "Condensed Imidazoles" in "The Chemistry of Heterocyclic Compounds", A. Weissberger and E. C. Taylor, eds., 1986, John Wiley & Sons; Adv. of Het. Chem., 36, 343/1984; Chem. Pharm. Bull., 22, 482/1974; J. Het. Chem., 12, 481/1975; Chem. Pharm. Bull., 22, 1814/1974; Ann., 660, 104/1962; Chem. Pharm. Bull., 23, 452/1975; J. Het. Chem., 10. 411/1973; and J. Chem. Soc. Perkin I, 2047/1977.

The compounds of general formula (I') are bases which form salts with organic and inorganic acids which salts can advantageously be used for isolation and purification.

The following Examples are given for the purpose of illustrating the present invention:

EXAMPLE 1

3-Amino-2-methoxypyrazolo[1,5-a]pyridine Hydrochloride

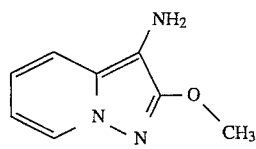

1.1  1.48 g. 2-methoxy-pyrazolo[1,5-a]pyridine (Bull. Chem. Soc. Jap., 49, 1980/1976) are dissolved with ice-cooling in 20 ml. concentrated nitric acid and mixed dropwise with 10.5 ml. fuming nitric acid. The reaction mixture is stirred for 30 minutes in an ice-bath and for 1 hour at ambient temperature. The reaction solution is poured on to ice, the precipitate obtained is filtered off with suction and washed with water. There is obtained 1 g. (52% of theory) 2-methoxy-3-nitropyrazolo[1,5-a]-pyridine; m.p. 213°–216° C.

1.2  0.8 g. of the nitro compound obtained in 1.1 is suspended in 80 ml. 2N hydrochloric acid and mixed with zinc dust while stirring vigorously. After repeated addition of zinc dust, after 1 hour a clear solution is obtained over a sediment of excess zinc dust. This is filtered off and the filtrate is adjusted to pH 7 with sodium hydroxide. The reaction mixture is extracted with ethyl acetate. The organic phase is evaporated and the remaining oil is filtered with ethanol over a short layer of silica gel. The eluate is evaporated, the residue is dissolved in diethyl ether and the ethereal solution is mixed with ethereal hydrochloric acid. The precipitate obtained is filtered off with suction and again recrystallised from isopropanol. There is obtained 0.33 g. (42% of theory) of the title compound; m.p. 238°–241° C.

TLC (silica gel, acetone/methylene chloride/glacial acetic acid 50:45:5 v/v/v)=$R_f$=0.6.

EXAMPLE 2

3-Amino-2-chloro-5,7-dimethylpyrazolo[1,5-a]pyrimidine Hydrochloride

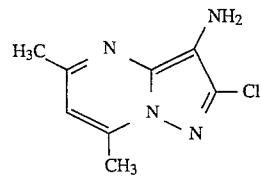

Analogously to Example 1, starting from 2-chloro-5,7-dimethylpyrazolo[1,5-a]pyrimidine (see Ann. Chem., 647, 116/1961), there is obtained 3-amino-2-chloro-5,7-dimethylpyrazolo[1,5-a]pyrimidine hydrochloride; m.p. 227°–230° C.

TLC (silica gel, acetone/methylene chloride/glacial acetic acid 50:45:5 v/v/v): $R_f$=0.8.

EXAMPLE 3

3-Amino-2-methylpyrazolo[1,5-a]pyridine Hydrochloride

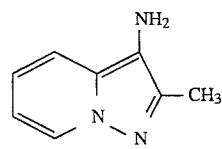

7 g. 3-Acetyl-2-methylpyrazolo[1,5-a]pyridine (see J. Org. Chem., 42, 443/1977) are dissolved in 140 ml. 6N hydrochloric acid and mixed dropwise at 0° C. with a solution of 5.52 g. sodium nitrite in water. After 2 hours, the ice-bath used for the cooling is removed and the reaction mixture is left to stand overnight at ambient temperature and then adjusted to pH 9. The precipitated nitroso compound (6.4 g.) is filtered off with suction and dissolved in about 150 ml. 2N hydrochloric acid. The nitroso compound is reduced with zinc dust analogously to Example 1.2. The crude product is chromatographed on silica gel with ethyl acetate. The product-containing fractions are evaporated, the residue is dissolved in ethanol and the solution is mixed with ethanolic hydrogen chloride. The precipitate which is obtained after some time is filtered off with suction and dried. There are obtained 3.1 g. (45% of theory) of the title compound; m.p. >275° C.; TLC (silica gel, ethyl acetate/acetone/glacial acetic acid/water 50:25:12.5:12.5 v/v/v/v): $R_f$=0.6.

EXAMPLE 4

3-Amino-2-methylpyrazolo[3,2-b]thiazole Hydrochloride

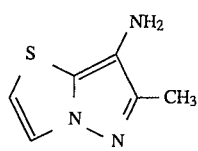

Analogously to Example 3, from 3-acetyl-2-methylpyrazolo[3,2-b]thiazole (see Chem. Pharm. Bull., 22, 482/1974) there is obtained 3-amino-2-methylpyrazolo-[3,2-b]thiazole hydrochloride; m.p. 215°–218° C.; TLC (silica gel, methanol): $R_f$=0,65.

EXAMPLE 5

3-Amino-2-methoxy-5,7-dimethylpyrazolo[1,5-a]pyrimidine Hydrochloride

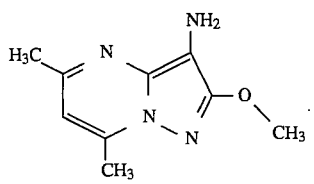

1.04 g. 2-Methoxy-5,7-dimethylpyrazolo[1,5-a]pyrimidine (see Ann. Chem., 647, 116/1961) are nitrosated analogously to Example 3. There is obtained 1.1 g. (91% of theory) of the corresponding 3-nitroso compound which is reduced with zinc dust analogously to Example 1.2. There is obtained 0.8 g. (80% of theory) of the title compound; m.p. 187°–190° C.

TLC (silica gel, acetone/methylene chloride/glacial acetic acid 50:45:5 v/v/v): $R_f$=0.6.

EXAMPLE 6

Analogously to Example 5, there are obtained the compounds set out in the following Table by nitrosation of the 3H-starting heterocyclic compound and reduction of the nitroso group.

The starting heterocyclic compound of Example 6b is described in J. Het. Chem., 12, 481/1975, those of Examples 6c) and 6d) in J. Het. Chem., 18, 1149/1981. The 3H-starting heterocyclic compound of Example 6a) is prepared analogously to the corresponding 2-methoxy compound in Example 1 by alkylation with ethyl bromoacetate (analogously to Bull. Chem. Soc. Jap., 49, 1980/1976).

TABLE

| Example No. | structure | m.p. | $R_f$[1] |
|---|---|---|---|
| 6a | (NH₂ pyrazolopyridine with –O–CH₂–C(O)–O–CH₂CH₃) | 179–184° C. | 0.75[2] |
| 6b | (NH₂ pyrazolopyridine with phenyl) | >240° C. | 0.75[3] |
| 6c | (NH₂ pyrazolopyridine with –C(O)OH) | >250° C. | 0.35[4] |
| 6d | (NH₂ pyrazolopyridine with –C(O)O–CH₂CH₃) | 205–213° C. | 0.6[5] |

[1] TLC on silica gel
[2] elution agent: acetone/methylene chloride/glacial acetic acid 50:45:5 v/v/v
[3] elution agent: methanol
[4] elution agent: ethyl acetate/acetone/glacial acetic acid/water 50:25:12.5:12.5 v/v/v/v
[5] elution agent: ethyl acetate

EXAMPLE 7

3-Amino-4-benzylpyrazolo[1,5-a]imidazole Dihydrochloride

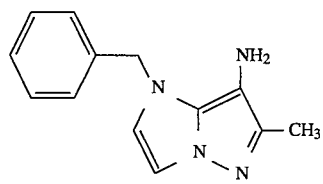

0.4 g. 4-Benzyl-3-nitrosopyrazolo[1,5-a]imidazole (see Chem. Pharm. Bull., 22, 482 1974) are reduced with zinc in hydrochloric acid analogously to Example 1.2 and converted with ethanolic hydrogen chloride into the dihydrochloride. There is obtained 0.37 g. (85% of theory) 3-amino-4-benzylpyrazolo[1,5-a]imidazole dihydrochloride; m.p. 158° C. (decomp.).

TLC (silica gel, acetone/methylene chloride/glacial acetic acid): $R_f$=0.4.

EXAMPLE 8

3-Amino-2-phenylpyrazolo[1,5-a]quinoline

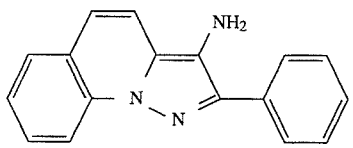

1.0 g. 2-Phenylpyrazolo[1,5-a]quinoline (see J. Het. Chem., 12, 481/1975) are nitrosated analogously to Example 3. There is obtained 1 g. (89% of theory) of the corresponding 3-nitroso compound which is suspended in 90 ml. ethanol and mixed with 200 mg. palladium on carbon. The mixture is heated to 80° C. and 0.25 ml. hydrazine hydrate added portionwise thereto. After 10 minutes, the palladium-carbon is filtered off and the filtrate is evaporated. The residue is dissolved in ethanol and mixed with ethanolic hydrogen chloride. The precipitated hydrochloride is filtered off with suction to give 0.7 g. (72% of theory) of the title compound; m.p. 255°–258° C. TLC (Silica gel/methylene chloride): $R_f$=0.2

EXAMPLE 9

3-Amino-2,4-dimethylpyrazolo[1,5-a]imidazole Dihydrochloride

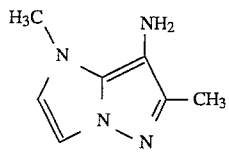

9.1 1.92 g. 1,2-Dimethylimidazole are dissolved in 10 ml. methylene chloride and mixed, while cooling with ice, with a solution of O-p-toluenesulphonyl hydroxylamine which is obtained by the reaction of 15.4 g. O-p-toluenesulphonyl acethydroxamic acid ethyl ester with 118 ml. 60% aqueous perchloric acid. The reaction mixture is stirred for 3 hours at ambient temperature. The precipitate obtained is filtered off and washed with diethyl ether. There are obtained 5 g. (88% of theory) N-amino-1,2-dimethylimidazolium-p-toluene-sulphonate.

9.2 5 g. of the product obtained in 9.1 are heated with 5.4 g. sodium acetate and 125 ml. acetic anhydride for 1 hour to 140° C. (bath temperature). The reaction mixture is evaporated in a vacuum and the residue is taken up in water. The pH value is adjusted to about 9 to 10 and then followed by extraction with methylene chloride. The organic phase is dried and evaporated and the residue is chromatographed on silica gel with ethyl acetate. There is obtained C.45 g. (11% of theory) 3-acetyl-2,4-dimethylpyrazolo[1,5-a]imidazole; m.p. 165°–167° C. 9.3 The compound obtained in 9.2 is nitrosated analogously to Example 3. There is obtained 0.35 g. (94% of theory) of the corresponding 3-nitroso compound (m.p. 179°–183° C.) which is dissolved in 100 ml. dilute aqueous sodium bicarbonate solution and reduced with sodium dithionite. The reaction mixture is evaporated and the residue is digested with ethanol. The ethanolic solution is evaporated and the product is precipitated out by the addition of ethereal hydrochloric acid. There is obtained 0.3 g. (80% of theory) of the title compound; m.p. 199°–204° C. (decomp.).

TLC (silica gel, ethyl acetate/acetone/glacial acetic acid/water 50:25:12,5:12,5 v/v/v/v): $R_f$=0.2.

EXAMPLE 10

3-Amino-2,4-dimethyl-6-phenylpyrazolo[3,2-c]-s-triazole Hydrochloride

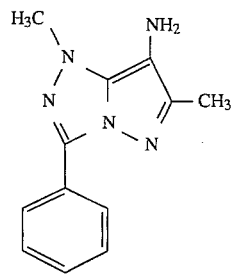

10.1 0.84 g. 2-Methyl-6-phenylpyrazolo[3,2-c]-s-triazole (see J. Chem. Soc. Perkin I, 2047/1977) are dissolved in 15 ml. dimethylformamide and mixed with 0.95 g. p-toluenesulphonic acid methyl ester. To this mixture is added portionwise 0.2 g. of 55% sodium hydride, followed by stirring for 1 hour at ambient temperature. The reaction mixture is poured on to ice and the mixture is extracted with ethyl acetate. There is obtained 1 g. of crude 2,4-dimethyl-6-phenylpyrazolo[3,2-c]-s-triazole. TLC (silica gel, methylene chloride/ethyl acetate 50:1 v/v): $R_f$=0.5.

10.2 To a solution of 1.8 g. 2,4-dimethyl-6-phenylpyrazolo[3,2-c]-s-triazole and 0.5 g. sodium acetate in 8 ml. glacial acetic acid is added portionwise phenyl diazonium tetrafluoroborate which was obtained by diazotisation of 2.2 ml. aniline. The reaction mixture is left to stand overnight, then diluted with water and the orange-yellow precipitate is filtered off with suction. The 3-phenylazo compound is purified by chromatography on silica gel with methylene chloride. Yield 1.3 g. (73% of theory); m.p. 183°–186° C.

10.3 1.3 g. 2,4-Dimethyl-6-phenyl-3-(phenylazopyrazolo[3.2-c]-s-triazole from 10.2 is suspended in a mixture of 100 ml. ethanol and 100 ml. diluted aqueous sodium bicarbonate solution and mixed with an excess of sodium dithionite. The reaction mixture is stirred for about 2 days at 60° C. During this time, further sodium dithionite, sodium bicarbonate and ethanol (1 liter) are added thereto.

The reaction mixture is evaporated and the residue is taken up in ethyl acetate. The organic phase is thoroughly washed with water, dried and evaporated. The residue is dissolved in ethanol and the hydrochloride is precipitated cut by the addition of ethanolic hydrogen chloride. There is obtained 0.8 g. of the title compound; m.p. 210°–213° C. TLC (silica gel, ethyl acetate/acetone/glacial acetic acid/water 50:25:12.5:12.5 v/v/v/v): $R_f$=0.7.

EXAMPLE 11

3-Amino-pyrazolo[1,5-b]pyridazine Hydrochloride

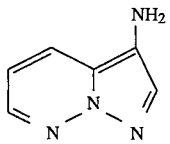

11.1 1.8 g. Pyrazolo [1,5-b]pyridazine-3-carboxylic acid ethyl ester (see Chem. Pharm. Bull., 22, 1814/1974) are boiled under reflux for 5 hours with 36 ml. 6N hydrochloric acid. The reaction mixture is evaporated and the residue is dissolved in water. The solution is neutralised with sodium carbonate and extracted three times with ethyl acetate. The organic phase is dried and evaporated. There is obtained 0.85 g. (75% of theory) of oily pyrazolo[1,5-b]pyridazine.

TLC (silica gel, methylene chloride/ethyl acetate 2:1 v/v): $R_f$=0.6.

11.2 0.8 g. of the compound obtained in 11.1 is nitrosated analogously to Example 8. There is obtained 0.6 g. (60% of theory) 3-nitrosopyrazolo[1,5-b]pyridazine; m.p. 129°–132° C.

The nitroso compound is reduced with palladium/hydrazine analogously to Example 8. There is obtained 0.4 g. (58% of theory) of the title compound; m.p. 230° C. (decomp.).

TLC (silica gel, ethyl acetate/methanol 1:1 v/v): $R_f$=0.6.

EXAMPLE 12

3-Amino-2,6-dimethylpyrazolo[1,5-a]pyrimidine Hydrochloride

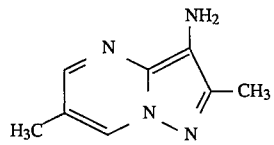

3.2 g. 2,6-Dimethyl-3-nitropyrazolo[1,5-a]pyrimidine (see Synthesis, 673/1982) are dissolved in 320 ml. ethanol and mixed with 320 ml. of a 5% aqueous solution of sodium bicarbonate. 14.2 g. Sodium dithionite are now added to this mixture portionwise with stirring and cooling until the thin layer chromatogram shows the absence of starting material. The reaction mixture is concentrated somewhat and extracted three times with ethyl acetate. The organic phase is dried and evaporated. The residue is dissolved in a little ethanol and mixed with an equimolar amount of hydrogen chloride in diethyl ether. The precipitated crystals are filtered off with suction. There are obtained 2.9 g. (80% of theory) of the title compound; m.p. 224° C. (decomp.).

TLC (silica gel, chloroform/methanol/methyl ethyl ketone/glacial acetic acid/water 75:35:25:5:8 v/v/v/v/v): $R_f$=0.73.

EXAMPLE 13

3-Amino-4-methyl-6-methylthio-2-phenylpyrazolo[3,2-c]-s-triazole Hydrochloride

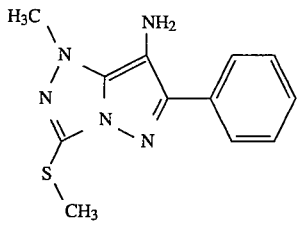

13.1 4.6 g. 6-Methylthio-2-phenylpyrazolo[3,2-c]-s-triazole (see J. Chem. Soc. Perkin I, 2047/1977) are dissolved in 46 ml. dry dimethylformamide and mixed with 4.4 g. p-toluenesulphonic acid methyl ester. 1 g. of approximately 55% sodium hydride are added portionwise thereto with stirring. The reaction mixture is stirred for 1 hour at ambient temperature and then poured on to ice/water. Extraction is carried out with ethyl acetate and the organic phase is dried and evaporated. The crude product is purified by chromatography on silica gel with methylene chloride/ethyl acetate (50:1 v/v). There is obtained 1.5 g. (30% of theory) of the N-4-methylated heterocyclic compound.

TLC (silica gel, methylene chloride/ethyl acetate 50:1 v/v): $R_f$=0.35.

13.2 1.2 g. of the compound obtained in 13.1 is dissolved in 36 ml. glacial acetic acid and mixed with 1.33 g. 4-methoxyphenyldiazonium tetrafluoroborate. After 2 hours, the same amount of the diazonium salt is again added thereto and the reaction mixture is stirred overnight.

The reaction mixture is diluted with water and the pH value is adjusted to 5 with a dilute aqueous solution of sodium hydroxide. The precipitate obtained is filtered off, washed with water and dried in a vacuum at 50° C. There is obtained 1.9 g. (100% of theory) of the corresponding 3-azo compound.

13.3 The azo compound obtained in 13.2 is suspended in 100 ml. glacial acetic acid and reduced by the addition of zinc dust. The excess zinc is filtered off and the reaction mixture is evaporated. For purification, the crude product is dissolved in 100 ml. dioxan and mixed with 1.5 g. di-tert.-butyl dicarbonate. The mixture is stirred for 2 hours, evaporated and the product obtained is chromatographed on silica gel with methylene chloride/ethyl acetate (100:0 to 90:10 v/v). The fractions which contain the desired N-tert.-butoxycarbonylated amino compound are combined, evaporated and the residue is suspended in 50 ml. ethanol. For the splitting off of the tert.-butoxycarbonyl radical, 50 ml. ethanolic hydrochloric acid are added thereto, followed by stirring at ambient temperature. The reaction mixture is evaporated to dryness, dissolved in hot ethanol, filtered and the filtrate is mixed with diethyl ether. The precipitate obtained is filtered off with suction. There is obtained 0.6 g. (40% of theory) of the title compound; m.p. 207°–210° C.

TLC (silica gel, ethyl acetate): $R_f$=0.65.

EXAMPLE 14

3-Amino-4-chloro-2-methoxypyrazolo[1,5-a]pyridine Hydrochloride

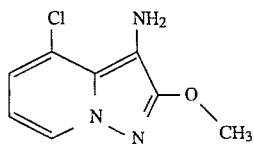

7.5 g. N-Amino-3-chloropyridinium mesitylene-sulphonate (see J. Chem. Soc. Perkin I, 258C/1973) are dissolved in 50 ml. dry dimethylformamide and mixed with 3.5 g. finely powdered potassium carbonate. 28 ml. of a 5M diketene solution in methylene chloride are added thereto with cooling. The reaction mixture is stirred for 30 minutes at 0° C. and for 2 hours at ambient temperature. The precipitate obtained is filtered off with suction, the filtrate is evaporated and the residue obtained is purified by chromatography on silica gel with methylene chloride/5–10% methanol. There are obtained 2.7 g. of the N-acetoacetylated compound which is dissolved in 100 ml. ethanol and mixed with 2.6 g. of finely powdered potassium carbonate. The reaction mixture is stirred for 2 days at ambient temperature and finally evaporated. The residue is dissolved in 100 ml. dry dimethylformamide, the solution is cooled and mixed with 7 g. methyl iodide. The reaction mixture is stirred for 1 hour at 0° C. and for 30 hours at ambient temperature. The dimethylformamide is distilled off and the residue is dissolved in water/ethyl acetate. The ethyl acetate phase is separated off, dried and evaporated. The product obtained is purified by column chromatography on silica gel with methylene chloride/ethyl acetate (20:1 v/v). There is obtained 0.8 g. 3-acetyl-4-chloro-2-methoxypyrazolo[1,5-a]-pyridine which is nitrosated and reduced analogously to Example 3. Yield: 0.3 g. of the title compound; m.p. 200°–230° C. (decomp.).

TLC (silica gel, methylene chloride/ethyl acetate 1:1 v/v): $R_f$=0.6.

EXAMPLE 15

3-Amino-2-methyl-5,6,7,8-tetrahydropyrazolo[3,2-b]-benzothiazole Hydrochloride

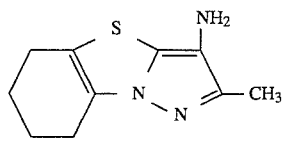

15.1 28.5 g. Acetamide and 21.3 g. phosphorus pentasulphide are suspended in 32 ml. anhydrous toluene and mixed, while stirring, with 5 ml. of a mixture of 85 g. 2-bromocyclohexanone and 40 ml. anhydrous toluene. The reaction mixture is heated to 75° to 80° C. and the remainder of the bromoketone solution is added thereto. The reaction mixture is boiled under reflux for 10 minutes, cooled and adjusted to pH 8 to 9 with a 2N aqueous solution of sodium hydroxide. Extraction is carried out with ethyl acetate, the organic phase is washed with water, dried and evaporated. The residue is distilled in a vacuum to give 14.4 g. 2-methyl-4,5,6,7-tetrahydrobenzothiazole. m.p. 62° C./0.5 mm.Hg.

15.2 2.06 g. 2-Methyl-4,5,6,7-tetrahydrobenzothiazole are dissolved in about 10 ml. methylene chloride, the mixture is cooled and mixed with 30 mMole of a methylene chloride solution of O-p-toluenesulphonyl-hydroxylamine. The reaction mixture is stirred for 2 hours on an ice-bath and the product is precipitated out by the addition of diethyl ether. There are obtained 6.45. (94% of theory) N-amino-2-methyl-4,5,6,7-tetrahydrobenzothiazolium-p-toluene-sulphonate; m.p. 127°–140° C.

15.3 6.2 g. of the N-amino compound obtained in 15.2 are, together with 4.7 g. sodium acetate and 16 ml. acetic anhydride, heated to 140° C. (bath temperature). After 1 hour, the mixture is evaporated, the residue is dissolved in water/methylene chloride, rendered alkaline with sodium carbonate and extracted three times with methylene chloride. The product obtained is purified by column chromatography on silica gel with ethyl acetate/ligroin (1:2 v/v). There are obtained 2.1 g. (50% of theory) 3-acetyl-2-methyl-5,6,7,8-tetrahydropyrazolo[3,2-b]benzothiazole; m.p. 90°–92° C.

15.4 1.4 g. of the compound obtained in 15.3 is nitrosated analogously to Example 3 and the nitroso compound is reduced. There is obtained 1.3 g. of the title compound; m.p. 239°–240° C. (decomp.).

TLC (silica gel, ethyl acetate): $R_f$=0.5.

EXAMPLE 16

3-Amino-2,5-dimethyl-6-phenylpyrazolo[3,2b]thiazole Hydrochloride

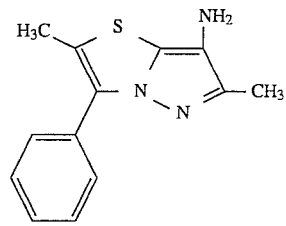

Analogously to Example 15, starting from α-bromopropiophenone, there is obtained the title compound; m.p. 252°–254° C. (decomp.).

TLC (silica gel, ethyl acetate): $R_f$=0.6

EXAMPLE 17

3-Amino-pyrazolo[1,5-a]pyridine Hydrochloride

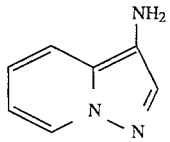

17.1 8.2 g. Pyrazolo [1,5-a]pyridine (see Ann. Chem., 498/1977) are dissolved in 30 ml. 6N hydrochloric acid, the solution is cooled to 0° C. and a solution of 6.9 g. sodium nitrite in 30 ml. water slowly added dropwise thereto. After 1 hour, the nitrosation is complete. About 100 ml. water are added thereto followed by repeated extraction with ethyl acetate. The organic phase is dried and evaporated. There are obtained 9.6 g. 3-nitrosopyrazolo[1,5-a]pyridine.

17.2 9 g. of the above-obtained nitroso compound are introduced into a solution of 22 g. stannous chloride dihydrate in 180 ml. concentrated hydrochloric acid. The reaction mixture is stirred for 1 hour at ambient temperature and, for the completion of the reduction, mixed with 8 g. stannous chloride dihydrate in 30 ml. concentrated hydrochloric acid. The suspension is poured on to about 150 g. ice, adjusted with sodium hydroxide to pH 12 and quickly extracted with ethyl acetate. The ethyl acetate phase is dried and evaporated. The residue obtained is dissolved in about 350 ml. diethyl ether and mixed with ethereal hydrochloric acid. The precipitate obtained is filtered off, washed with diethyl ether and dried. There are obtained 11.3 g. (100% of theory) of the title compound; m.p. 228°–232° C.

TLC (silica gel, ethyl acetate/methanol 9:1 v/v): $R_f$=0.52.

EXAMPLE 18

3-Amino-2-methylthiopyrazolo[1,5-a]pyridine Hydrochloride

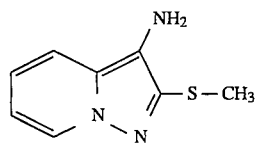

4 g. 2-Methylthio-3-nitropyrazolo[1,5-a]pyridine (see Heterocycles, 6, 379/1977; Chem. Pharm. Bull., 25 1528/1977) are dissolved in 200 ml. concentrated hydrochloric acid and mixed with 20 g. stannous chloride dihydrate. After 1 hour, there are again added 15 g. stannous chloride dihydrate, 15 ml. concentrated hydrochloric acid and 200 ml. water. After a further reaction period of 1 hour, the reaction mixture is poured on to ice, the yellow solution is rendered alkaline and extracted with ethyl acetate. The organic phase is dried and evaporated, the residue is dissolved in a little ethanol and mixed with ethereal hydrochloric acid in order to form the hydrochloride. There are obtained 3.9 g. (95% of theory) of the title compound; m.p. 226° C.

TLC (silica gel, methylene chloride/tert.-butyl methyl ether 2:8 v/v): $R_f$=0.6.

EXAMPLE 19

R,S-3-Amino-2-(1-hydroxyethyl)-pyrazolo[1,5-a]pyridine Hydrochloride

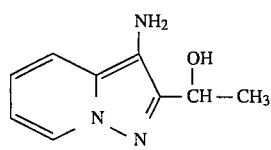

25 g. N-aminopyridine hydroiodide are dissolved in 250 ml. dry dimethylformamide and mixed, while stirring, with 17.5 g. potassium carbonate. Subsequently, while stirring, 20.5 g. R,S-2-hydroxy-5-oxobut-3-yne (see J. Chem. Soc. Perkin I, 1908/1972) are added dropwise thereto. The reaction mixture thereby warms up and is left to stand overnight. After the addition of 1.25 liters of water, the reaction mixture is extracted several times with ethyl acetate. The combined extracts are dried and evaporated. The remaining oil is diluted with some diethyl ether. After some time, precipitated crystals are filtered off with suction. There are obtained 9.8 g. (42% of theory) R,S-3-acetyl-2-(1-hydroxyethyl)-pyrazolo[1,5-a]pyridine ($R_f$ (silica gel, methylene chloride/ethyl acetate 1:1 v/v)=0.35) which is nitrosated analogously to Example 3. The nitroso compound is reduced analogously to Example 8 with palladium-carbon/hyrazine hydrate. There are obtained 6.8 g. of the title compound, the crystals of which contain 1.8 mole hydrogen chloride and melt at 229°–231° C. (decomp.). $R_f$ (silica gel, ethyl acetate/methanol 3:1 v/v)=0.65.

EXAMPLE 20

3-Amino-2,5-dimethyl-7-(dimethylamino)-pyrazolo[1,5-a]-pyrimidine Hydrochloride

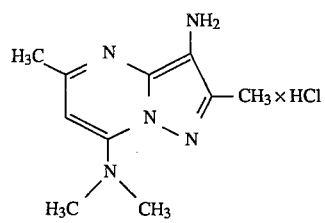

20.1 1.6 g. 2,5-Dimethyl-7-hydroxypyrazolo[1,5-a]-pyrimidine are heated under reflux for 40 minutes with 16.6 ml. phosphorus oxychloride and 0.8 ml. N,N-dimethylaniline. Excess phosphorus oxychloride is distilled off and the residue is poured on to ice. Extraction is carried out with methylene chloride, the organic phase is washed with an aqueous solution of sodium carbonate, dried and evaporated. The residue obtained is dissolved in 28 ml. ethanol and mixed with 2 g. of a 40% solution of dimethylamine in water. The mixture is stirred for 2.5 hours at ambient temperature, evaporated and the residue chromatographed over silica gel with ethyl acetate. There is obtained 0.86 g. (46% of theory) 2,5-dimethyl-7-(N,N-dimethylamino)pyrazolo[1,5-a]pyrimidine which is nitrosated analogously to Example 3. The nitroso compound is reduced analogously to Example 8 with palladium-carbon/hydrazine hydrate. There is obtained 0.8 g. of the title compound. $R_f$ (silica gel, chloroform/methanol/methyl ethyl ketone/glacial acetic acid/water 75:35:25:5:8 v/v/v/v/v)-0.54.

EXAMPLE 21

3-Amino-4-methylpyrazolo[1,5-a]imidazole Hydrochloride

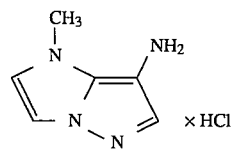

21.1 Analogously to the process described in "Organikum" (pub. VEB Deutscher Verlag der Wissenschaften, Berlin, pp. 514–515), 65 g. ethyl ethoxymethylenecyanoacetate are reacted with 55 g. 2,2-diethoxyethylhydrazine to give 100.2 g. 5-amino-1-(2,2-diethoxyethyl)-pyrazole-4-carboxylic acid which is dissolved in 4 liters ethanol and mixed with 2 liters 20% sulphuric acid. The reaction mixture is heated under reflux for 3 hours and neutralised by the addition of solid sodium bicarbonate. Precipitated salt is filtered off and the filtrate is evaporated. The residue is extracted several times with boiling methylene chloride and the extracts are combined and evaporated to give 58.2 g. (86% of theory) pyrazolo[1,5-a]imidazole-3-carboxylic acid ethyl ester; m.p. 126°–127° C.

$R_f$ (silica gel, ethyl acetate)=0.64.

21.2 18.7 g. of the above-obtained carboxylic acid ester are dissolved in 190 ml. dimethylformamide and mixed with 17 g. p-toluenesulphonic acid methyl ester. While stirring, 3.98 g. 55% sodium hydride are introduced portionwise. The reaction mixture is stirred for 30 minutes at ambient temperature, then poured on to ice/water and extracted with ethyl acetate. There are obtained 21.9 g. (100% of theory) 4-methylpyrazolo[1,5-a]imidazole-3-carboxylic acid ethyl ester which is saponified by boiling with 600 ml. concentrated hydrochloric acid. The resultant carboxylic acid is simultaneously decarboxylated to give 16.7 g. (83% of theory) 4-methylpyrazolo[1,5-a]imidazole dihydrochloride ($R_f$=0.39, silica gel, methylene chloride with 5% by volume of methanol).

21.3 12.8. g. Aniline are diazotised in a solution of 12.8 ml. concentrated sulphuric acid in 64 ml. water by the addition of a solution of 9.5 g. sodium nitrite in 42 ml. water. The solution is adjusted to pH 5 by the addition of sodium hydroxide and mixed dropwise at 5 to 10° C. with a solution of 16.5 g. of the above-obtained 4-methylpyrazolo[1,5-a] imidazole dihydrochloride in 165 ml. water and 14 ml. glacial acetic acid. The reaction mixture is stirred for 1 hour at 5° to 10° C. and then for 3 hours at ambient temperature, whereafter the separated precipitate is filtered off with suction. There are obtained 12 g. 4-methyl-3-phenylazopyrazolo[1,5-a]imidazole which is reduced with sodium dithionite analogously to Example 10.3 and purified analogously to Example 13.3. There are obtained 3.3 g. 3-amino-4-methylpyrazolo[1,5-a]imidazole hydrochloride; m.p. 210° C. (decomp.).

$R_f$=0.23 (silica gel, ethyl acetate/acetone/glacial acetic acid/water 50:25:12.5:12.5).

EXAMPLE 22

3-Amino-2,4,6-trimethylpyrazolo[3,2-c]-s-triazole Hydrochloride

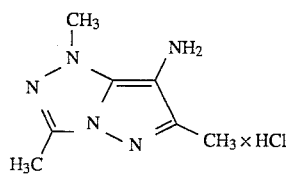

22.1 Starting from 4-ethoxycarbonyl-3-methylpyrazol-5-yl hydrazine (see Chem. Ber., 89, 2552/1956), there is prepared, in the manner described in Example 6 of published Federal Republic of Germany Patent Specification No. 18 10 462, 2,6-dimethyl-4H-pyrazolo[3,2-c]-s-triazole-3-carboxylic acid ethyl ester, which, before acidic saponification, is methylated analogously to Example 10.1. As intermediate, there is thus obtained 2,4,6-trimethylpyrazolo[3,2-c]-s-triazole-3-carboxylic acid ethyl ester ($R_f$=0.52; silica gel, ethyl acetate/ligroin 1:1 v/v) which is saponified by boiling with concentrated hydrochloric acid and simultaneously decarboxylated. There is obtained 2,4,6-trimethylpyrazolo[3,2-c]-s-triazole ($R_f$=0.24; silica gel, ethyl acetate/ligroin 1:1 v/v) as a pale yellowish oil which crystallises after some time.

22.2 Analogously to Example 13.2 and 13.3, the above-obtained product is reacted with p-methoxybenzenediazonium salt, reduced and the product obtained purified. The title compound is obtained; m.p. 240° C.

$R_f$=0.50 (silica gel, ethyl acetate/acetone/glacial acetic acid/water 50:25:12.5:12.5 v/v/v/v).

EXAMPLE 23

2-Acetamido-3-amino-pyrazolo[1,5-a]pyridine Hydrochloride

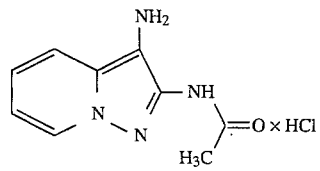

4 g. 2-Acetamidopyrazolo[1,5-a]pyridine (see Chem. Pharm. Bull., 21, 2146/1973) are nitrosated analogously to Example 3. The nitroso compound obtained is reduced with palladium-carbon/hydrazine hydrate analogously to Example 8. There are obtained 3.9 g. (67% of theory) 2-acetamido-3-aminopyrazolo[1,5-a]pyridine hydrochloride; m.p. 255°–259° C. (decomp.).

$R_f$=0.5 (silica gel, ethyl acetate/acetone/glacial acetic acid/water 50:25:12.5:12.5 v/v/v/v).

EXAMPLE 24

2-Vinyl-3-aminopyrazolo[1,5-a]pyridine Hydrochloride

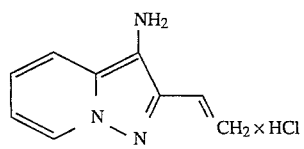

25 g. R,S-3-Acetyl-2-(1-hydroxyethyl)-pyrazolo[1,5-a] pyridine (from Example 22) are mixed with 50 ml. concentrated sulphuric acid and heated for 2 hours at a bath temperature of 95° C. The reaction mixture is poured on to a large quantity of ice, rendered alkaline with sodium hydroxide and extracted with ethyl acetate. The crude product obtained is chromatographed over silica gel with ligroin/ethyl acetate (95:5 to 90:10 v/v). There are obtained 3.4 g. 2-vinylpyrazolo[1,5-a]pyridine ($R_f$=0.6; silica gel, ligroin/ethyl acetate 3:1 v/v), which is reacted with phenyldiazonium salt analogously to Example 21.2, reduced and purified. The title compound is obtained.

$R_f$=0.65; silica gel, ligroin/acetone/glacial acetic acid 50:45:5 v/v/v).

EXAMPLE 25

6-(3-Acetoxypropyl)-3-amino-2-methylpyrazolo[1,5-a]pyrimidine

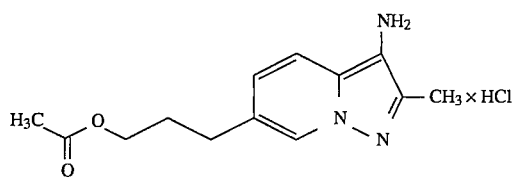

By the reduction of 6-(3-acetoxypropyl)-2-methyl-3-nitropyrazolo[1,5-a]pyrimidine (see Synthesis, p. 673/1982) analogously to Example 12, there is obtained the title compound.

$R_f$=0.21 (silica gel, methylene chloride/methanol 90:1 v/v).

EXAMPLE 26

2,3-Diaminopyrazolo[1,3-a]pyridine Dihydrochloride

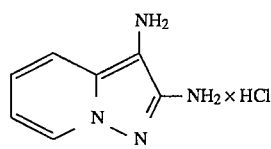

2.66 g. 2-aminopyrazolo[1,5-a]pyridine (see Chem. Pharm. Bull., 21, 2146/1973) are reacted with p-methoxybenzenediazonium salt analogously to Example 13.2. The resultant azo compound is reduced with sodium dithionite analogously to Example 10.3 and the crude product obtained is purified analogously to Example 13.3. There is obtained the title compound; m.p. 190° C.

$R_f$=0.6 (silica gel, ligroin/acetone/glacial acetic acid 60:40:1 v/v/v).

EXAMPLE 27

3-Aminopyrazolo[3,2-b]thiazole Hydrochloride

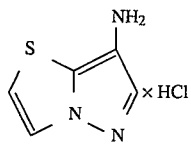

27.1 60 g. of the potassium salt of dithiocarbazinic acid 2,2-diethoxyethyl ester are reacted with 60 ml. bromoacetaldehyde diethyl acetal in 400 ml. dimethylformamide at a bath temperature of 50° C. for 12 hours. The reaction mixture is evaporated, the remaining emulsion is mixed with 500 ml. water and the product is extracted with diethyl ether. The crude product is purified by chromatography over silica gel (diethyl ether/ligroin 6:4 v/v). There are obtained 20.9 g. of the dithiocarbazinic acid 2,2-diethoxyethyl ester. 27.2 17.75 g. of the above-obtained carbazinic acid ester and 11.3 g. formyl chloroacetic ester are dissolved in 250 ml. ethanol and heated for 2 hours at 50° C. The reaction mixture is evaporated, the residue is mixed with water and the product is extracted with diethyl ether. The ethereal phase is dried and evaporated. The residue is heated under reflux for 4 hours in 300 ml. ethanolic hydrochloric acid. The reaction mixture is evaporated, the residue is taken up in water and the reaction product is extracted with ethyl acetate. For purification, it is chromatographed over silica gel with ethyl acetate/ligroin (1:1 v/v). There are obtained 6.5 g. pyrazolo[3,2-c]thiazole-3-carboxylic acid ethyl ester.

$R_f$=0.65 (silica gel, toluene/dioxan/glacial acetic acid 72:20:8 v/v/v).

27.3 5.8 g. of the above-obtained ester are heated under reflux for 7 hours in a mixture of 300 ml. 3N hydrochloric acid and 15 ml. dioxan, whereby, every 2 hours, in each case 15 ml. concentrated hydrochloric acid are added thereto. The reaction mixture is adjusted to pH 8 by the addition of sodium hydroxide and extracted several times with ethyl acetate. After drying and evaporating the organic phase, there are obtained 3 g. pyrazolo[3,2-c]thiazole in the form of a yellowish oil. This product is nitrosated analogously to Example 3 and reduced. Where are obtained 3.4 g. of the title compound as dihydrochloride; m.p. 170° C. (decomp.).

$R_f$=0,66 (silica gel, ethyl acetate/acetone/glacial acetic acid/water 50:25:12.5:12.5 v/v/v/v).

EXAMPLE 28

3-Amino-4,6-dimethylpyrazolo[3,2-c]-s-triazole Hydrochloride

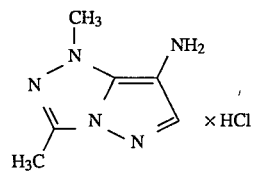

28.1 24.4 g. 3-Aminopyrazole-4-carboxylic acid ethyl ester (see Organikum, p. 514, pub. VEB Verlag der Wissenschaften, Berlin) are suspended in 100 ml. concentrated hydrochloric acid and diazotised at 0° to 5° C. by the addition of a solution of 10.35 g. sodium nitrite in 50 ml. water. Thereafter, a solution of 100 g. stannous chloride in 100 ml. concentrated hydrochloric acid is added thereto and the reaction mixture is stirred for 2 hours in an ice-bath. The yellow precipitate obtained is filtered off, dissolved in 150 ml. water and mixed with 20 ml. acetic anhydride. The reaction mixture is heated to a bath temperature of 80° C. and mixed portionwise over the course of 2 hour with, in all, 25 g. sodium bicarbonate. The neutral solution is then continuously extracted with ethyl acetate for 24 hours. After drying and evaporating the organic phase, there are obtained 17 g. 3-acethydrazinopyrazole-4-carboxylic acid ethyl ester ($R_f$=0.33; silica gel, acetone/methylene chloride/glacial acetic acid 50:45:5 v/v/v) which is cyclised with phosphorus oxychloride analogously to the procedure described in Example 6 of published Federal Republic of Germany Patent Specification No. 18 10 462. There are obtained 4.8 g. (32% of theory) 6-methylpyrazolo[3,2-c]-s-triazole-3-carboxylic/acid ethyl ester ($R_f$=0.70; silica gel, toluene/ethyl acetate/methanol 2:1:1 v/v/v). 28.2 Analogously to Example 10.1, the above-obtained heterocyclic compound is methylated and the product purified by chromatography over silica gel with ethyl acetate/ligroin (2:1 v/v). By heating for 6 hours with 6N hydrochloric acid, the ester is saponified and the carboxylic acid formed as intermediate is decarboxylated. The acid is neutralised by the addition of sodium carbonate and the product is extracted with ethyl acetate. There is obtained 1.1 g. of oily 4,6-dimethylpyrazolo-[3,2-c]-s-triazole ($R_f$=0.26; silica gel, ethyl acetate/ligroin 1:1 v/v).

28.3 The above-obtained heterocyclic compound is nitrosated analogously to Example 3 and the nitroso group is reduced with palladium-carbon/hydrazine analogously to Example 8. The title compound is obtained as hydrochloride; m.p. 190° C. (decomp.).

$R_f$=0.53 (silica gel; ethyl acetate/acetone/glacial acetic acid/water 50:25:12.5:12.5 v/v/v/v).

EXAMPLE 29

3-Amino-2-hydroxymethylpyrazolo[1,5-a]pyridine Hydrochloride

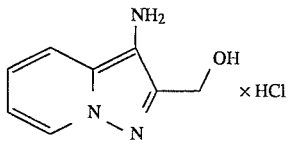

29.1. 10.5 g. Pyrazolo[1,5-a]pyridine-2-carboxylic acid ethyl ester (see J. Het. Chem., 18. 1149/1981) are dissolved in tetrahydrofuran and added to a suspension of 5 g. sodium aluminium hydride in dry tetrahydrofuran. The reaction mixture is heated under reflux for 3 hours and then poured into a mixture of ice and methanol. The mixture is mixed with 100 ml. 10% ammonium chloride solution and extracted with ethyl acetate. The organic phase is dried and evaporated. The residue is purified by chromatography on silica gel; with ligroin/ethyl acetate. There are obtained 7.3 g. 2-hydroxymethylpyrazolo[1,5-a]pyridine in the form of a yellow oil ($R_f$=0.49, silica gel, ethyl acetate).

29.2 The above-obtained compound is nitrosated analogously to Example 3 and reduced with palladium-carbon/hydrazine hydrate analogously to Example 8. There is obtained the title compound; m.p. 218° C. $R_f$=0.62 (silica gel, ethyl acetate/methanol 2:1 v/v).

EXAMPLE 30

3-Amino-2-chloropyrazolo[1,5-a]pyridine Hydrochloride

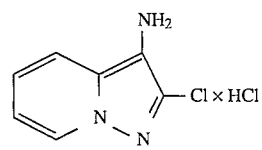

2-Aminopyrazolo[1,4-a]pyridine (see Chem. Parm. Bull., 21, 2146/1973) is reacted with p-methoxybenzene diazonium salt analogously to Example 13.2. 0.53 g of the 3-azo compound obtained is suspended in 10 ml. 6N hydrochloric acid and mixed at +5° C., while stirring, with a solution of 104 mg. sodium nitrite in 0.2 ml. water. After 30 minutes, a cold solution of 198 mg. cuprous chloride in 6 ml. 6N hydrochloric acid is added thereto and the reaction mixture is stirred for 40 hours at ambient temperature. The mixture is mixed with water and extracted three or four times with ethyl acetate. After purification of the crude product by chromatography over silica gel (elution agent: ethyl acetate/ligroin 1:1 v/v), there are obtained 320 mg. of 2-chloro-3-(p-methoxyphenylazo)pyrazolo[1,5-a]pyridine ($R_f$=0.65; silica gel, ethyl acetate/ligroin 1:1 v/v) which is reduced with sodium dithionite analogously to Example 10.3. There is obtained the title compound; m.p. 249°–251° C. (decomp.).

$R_f$=0.2 (silica gel, ethyl acetate/ligroin 1:1 v/v).

EXAMPLE 31

Analogously to Example 17, starting from the indicated substituted pyridines, there are obtained the compounds shown in the following Table:

| | starting material | product | m.p. | $R_f$ |
|---|---|---|---|---|
| 31.1 | ![pyridine-CH2OH] | ![product with NH2, CH2OH, xHCl] | 208° C. | 0.18[1] |
| 31.2 | ![pyridine-CH2OH]  Chem. Ber., 89, 2986/1956 | ![product with HO, NH2, xHCl] | 212° C. | 0.23[1] |

[1] ethyl acetate/methanol (9:1 v/v)

EXAMPLE 32

3-Amino-2-morpholinopyrazolo[1,5-a]pyridine Hydrochloride

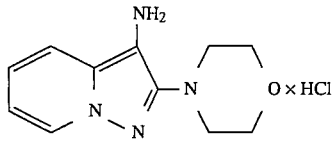

2-Aminopyrazolo[1,5-a]pyridine (see Chem. Pharm. Bull., 21, 2146/1973) is reacted with p-methoxybenzenediazonium salt analogously to Example 13.2. 4 g. of the azo compound obtained are dissolved in 100 ml. dimethylformamide and mixed with 5.33 g. β,β'-dibromodiethyl ether and 2 g. 55% sodium hydride. The reaction mixture is stirred for 1.5 hours at ambient temperature and water and ethyl acetate added thereto. The organic phase is separated off and the aqueous phase is again extracted with ethyl acetate. The combined organic phases are dried and evaporated. The residue is triturated with hexane. There are obtained 4.75 g. 3-(4-methoxyphenyl)-azo-2-morpholinopyrazolo[1,5-a]pyridine ($R_f$=0.7; silica gel, ethyl acetate/methylene chloride 1:1 v/v).

The azo compound is reduced with zinc in glacial acetic acid analogously to Example 13.3, purified and the tert.-butoxycarbonyl radical is split off with hydrochloric acid in ethanol. There are obtained 2.43 g. of the title compound; m.p. 105°–110° C. (decomp.). $R_f$=0.4 (silica gel, ethyl acetate).

EXAMPLE 33

Determination of Hydrogen Peroxide in Aqueous Solution

Reagent Solutions

Solution A
12 mg. peroxidase (=3000 U)
1 ml. 0.1N phosphate buffer, pH 8
Solution B
53.6 mg. 2,4,6-tribromohydroxybenzoic acid
1 ml. 0.1N phosphate buffer, pH 8
Solution C
32.1 mg. N-methyl-N-phenylaminomethanephosphonic acid hydrochloride (prepared according to published European Patent Specification No. A-0,175,250
1 ml. 0.1N phosphate buffer, pH 8

$4.8 \times 10^{-7}$ mole of a pyrazolo derivative useable according to the present invention are dissolved in about 5 to 9 ml. 0.1N phosphate buffer (pH 8), possibly with the help of a little methanol, acetone or dimethylformamide. To this are added 50 μl. of Solution A and, depending upon the desired coupler, either 200 μl. of Solution B or C. Finally, there are added thereto also 20 μl. of a 0.012 molar solution of hydrogen peroxide in water, then made up with buffer to 10 ml. and the solutions well mixed up. The solutions are measured in 1 cm. cuvettes. In the following Table 1, there are set out the wavelengths and the extinction at $\lambda_{max}$ of the resultant coloured materials.

TABLE 1

| substance from Example No. | coupling component TBHB[1] $\lambda_{max}$ [nm] | ext[3] | coupling component aniline[2] $\lambda_{max}$ [nm] | ext[3] |
|---|---|---|---|---|
| 1 | 568 | 69300 | 620 | 78200 |
| 2 | 536 | 18000 | 578 | 12600 |
| 3 | 622 | 28900 | 657 | 34800 |
| 4 | 572 | 30400 | 613 | 35600 |
| 5 | 557 | 36300 | 587 | 41900 |
| 6.1 | 568 | 39300 | 615 | 48800 |
| 6.2 | 628 | 19400 | 658 | 23000 |
| 6.3 | 602 | 22200 | 634 | 32600 |
| 6.4 | 587 | 7600 | 628 | 13300 |
| 7 | 626 | 30100 | 674 | 113300 |
| 8 | 613 | 13700 | 638 | 24200 |
| 9 | 617 | 45200 | 668 | 55500 |
| 10 | 613 | 39600 | 652 | 53300 |
| 11 | 504 | 10200 | 539 | 12600 |
| 12 | 542 | 39600 | 596 | 42000 |
| 13 | 612 | 25000 | 657 | 32600 |
| 14 | 577 | 42400 | 623 | 39300 |
| 15 | 594 | 34400 | 638 | 34000 |
| 16 | 592 | 34200 | 638 | 27400 |
| 17 | 572 | 53100 | 606 | 74600 |
| 18 | 635 | 31600 | 675 | 84600 |
| 19 | 613 | 22670 | 650 | 18160 |
| 20 | | | 639 | |
| 21 | 588 | 76290 | 633 | 94150 |
| 22 | 607 | 9300 | 648 | 42350 |
| 23 | 638 | 61500 | 658 | 66900 |
| 24 | 629 | 17950 | 660 | 28850 |
| 26 | 631 | 34620 | 683 | 35220 |
| 27 | 552 | 28940 | 585 | 39450 |
| 28 | 564 | 24210 | 604 | 41760 |
| 29 | 613 | 24870 | 648 | 37780 |
| 30 | 593 | 13990 | 631 | 22850 |
| 31.1 | 590 | 40970 | 623 | 51170 |
| 31.2 | 587 | 36950 | 619 | 46620 |
| 32 | 656 | 48450 | 709 | 134420 |

[1]TBHB = 2,4,6-tribromo-3-hydroxybenzoic acid
[2]aniline = N-methyl-N-phenylaminomethanephosphonic acid hydrochloride
[3]ext = extinction in [liter/mole cm$^2$]

EXAMPLE 34

Determination of Creatinine a) Indicator System
2,4,6-tribromo-3-hydroxybenzoic Acid/compound from Example 4

Reagent I:
100 mM tris buffer, pH 7.9
200 mM potassium chloride
0.25% detergent (Triton X 100®)
5 mM sodium cholate
10 mM ammonium chloride
5 mM magnesium chloride
15 mM 2,4,6-tribromo-3-hydroxybenzoic acid
15 U/ml. creatinine iminohydrolase (E.C. 3.5.4.21)
0.5 U/ml. N-methylhydantoinase (published Federal Republic of Germany Patent Specification No. A-3406770)
3 U/ml. sarcosine oxidase (E.C. 1.5.3.1)
3 U/ml. peroxidase (E.C. 1,11.1.7)
Reagent II:
20 mM potassium phosphate buffer, pH 6.0
100 mM ATP
3 mM compound from Example 4

40 U/ml. N-carbamoylsarcosine hydrolase (published Federal Republic of Germany Patent Specification No. A-3248145)

Sample material:

Aqueous creatinine standard solutions (2 to 20 mg./dl. creatinine).

Test batch and carrying out:
wavelength: 569 nm
layer thickness: 10 mm.
temperature: 25° C.
incubation time: 10 minutes
Pipetting scheme:
Reagent I: 1.00 ml.
Reagent II: 50 μl.
sample: 20 μl.

Measurement against reagent blank (water instead of standard solution as sample).

The results obtained are set out in the following Table:

| standard concentration (mg./dl.) | absorption (mE) |
| --- | --- |
| 2 | 92 |
| 4 | 194 |
| 6 | 272 |
| 8 | 368 |
| 10 | 472 |
| 12 | 565 |
| 14 | 658 |
| 16 | 753 |
| 18 | 841 |
| 20 | 974 | b) Indicator System
N-methyl-N-phenylaminomethanephosphonic Acid (MPA)/compound from Example 4

Reagent I:

Composition as in the case of Reagent I in a) but with 2 mM MPA (prepared according to published European Patent Specification No. A-0,175,250) instead of 15 mM 2,4,6-tribromo-3-hydroxybenzoic acid.

Reagent II:

Composition identical with Reagent II in a)

Sample material:

Aqueous standard solution (2 to 20 mg./dl. creatinine)

Test batch and carrying out:

Layer thickness, temperature, incubation time, pipetting scheme and measurement as in a). Wavelength: 620 nm.

The results obtained are set out in the following Table:

| standard concentration (mg./dl.) | absorption (mE) |
| --- | --- |
| 2 | 61 |
| 4 | 125 |
| 6 | 184 |
| 8 | 249 |
| 10 | 307 |
| 12 | 369 |
| 14 | 429 |
| 16 | 491 |
| 18 | 554 |
| 20 | 615 | c) Indicator System
N-ethyl-N-3-sulpho-2-hydroxypropyl-m-anisidine (ADOS)/compound from Example 4

Reagent I:

Composition as in the case of Reagent I in a) but with 2 mM ADOS (see Chem. Pharm. Bull., 30, 2492/1982) instead of 15 mM 2,4,6-tribromo-3-hydroxybenzoic acid.

Reagent II:

Composition identical with Reagent II in a).

Sample material:

Aqueous standard solutions (2 to 20 mg./dl. creatinine).

Test batch and carrying out:

Layer thickness, temperature, incubation time, pipetting scheme and measurement as in a) Wavelength: 598 nm.

The results obtained are set out in the following Table:

| standard concentration (mg./dl.) | absorption (mE) |
| --- | --- |
| 2 | 48 |
| 4 | 107 |
| 6 | 165 |
| 8 | 227 |
| 10 | 280 |
| 12 | 338 |
| 14 | 386 |
| 16 | 450 |
| 18 | 500 |
| 20 | 565 |

EXAMPLE 35

Determination of Glucose in Serum or Whole Blood by Means of a Test Carrier

The reagents necessary for the detection are incorporated into a film coating mass according to published European Patent Specification No. A-0,016,387:
0.2 mole/liter phosphate buffer, pH 5.5
0.2 mMole/liter sompound of Example 3
1.0 mMole/liter anilinemethane phosphonic acid (according published European Patent Specification No. A-0,175, 250)
1.0 KU/liter glucose oxidase
10.0 KU/liter peroxidase.

The film mass is raked out with a layer thickness of 150 μm. on paper as a porous carrier. For the film formation, the mass is left to dry for about minutes at 50° C.

For the determination of the glucose concentration (0 to about 35 mMole/liter) of serum or whole blood applied to the film, after about 1 minute the remission is measured on one side by means of a photometer. As the following Table of values shows, a precise determination of the glucose concentration can readily be carried out via a previously produced calibration curve.

| Table of values | |
| --- | --- |
| glucose (mg./dl.) | remission (%) |
| 0 | 93 |
| 11 | 91 |
| 103 | 71 |

-continued

Table of values

| glucose (mg./dl.) | remission (%) |
|---|---|
| 205 | 51 |
| 302 | 39 |
| 400 | 31 |
| 506 | 25 |
| 598 | 21 |

EXAMPLE 36

Determination of Hydrogen Peroxide in an Aqueous Solution

Reagent Solutions 1.75 mMole/liter compound from Example 19
2.0 mMole/liter anilinemethanephosphonic acid (according to published European Patent Specification No. A-0,175,250)
1.25 KU/liter peroxidase (activity determination with tetramethylbenzidine)
100 mMole/liter phosphate buffer, pH 5.5.

For the production of a calibration curve, 2.28 ml. of phosphate buffer are placed in 1 cm. cuvettes and, in each case, 100 µl. of compound from Example 22 and anilinomethanephosphonic acid, as well as 10 µl. peroxidase solution pipetted therein. The sample solution is obtained by the addition of 10 µl. of a definite hydrogen peroxide solution. The reference solution is obtained by the addition of the same volume of phosphate buffer. In each case, 30 seconds after the addition of the hydrogen peroxide, the extinction is measured of the coloured material formed by oxidative coupling as function of the amount of peroxide used at $\lambda_{max}$=660 nm at 25° C., using an Uvikon apparatus.

The values summarised in the following Table are in accordance with the Lamber-Beer Law over the whole of the measurement range. The correlation coefficient of the regression lines amounts to 0.99985. The hydrogen peroxide solutions used correspond to glucose concentrations in the diagnostic relevant range of from 30 mg./dl. to 600 mg./dl.

TABLE

Extinction values of the coupling product as function of the hydrogen peroxide concentration

| mMole/liter hydrogen peroxide | extinction |
|---|---|
| 1.74 | 0.132 |
| 3.48 | 0.232 |
| 6.96 | 0.448 |
| 10.44 | 0.622 |
| 13.92 | 0.858 |
| 17.40 | 1.051 |
| 20.88 | 1.253 |
| 24.36 | 1.463 |
| 27.84 | 1.635 |
| 31.32 | 1.842 |
| 34.80 | 2.061 |

It will be understood that the specification and examples are illustrative but not limitative of the present invention and that other embodiments within the spirit and scope of the invention will suggest themselves to those skilled in the art.

We claim:

1. A 3-amino pyrazolo heterocyclic derivative of the formula (II') to (IX')' as follows:

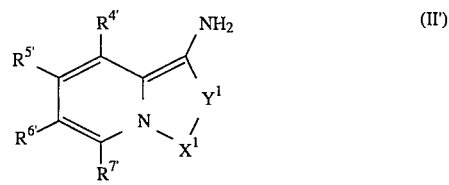

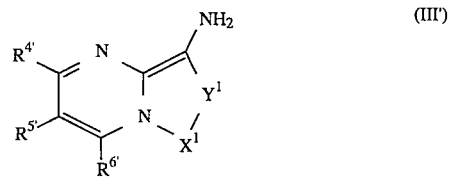

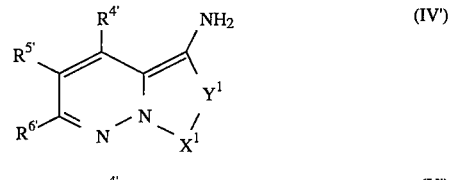

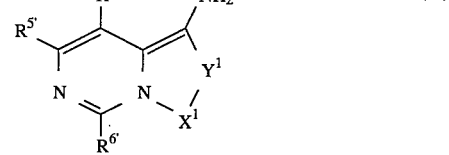

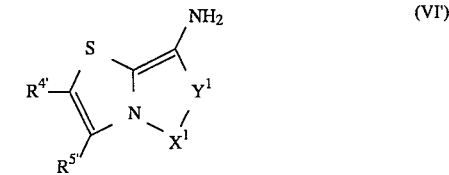

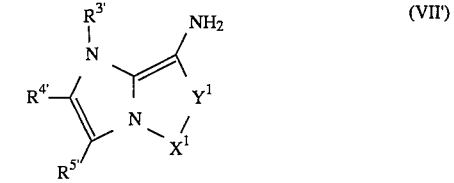

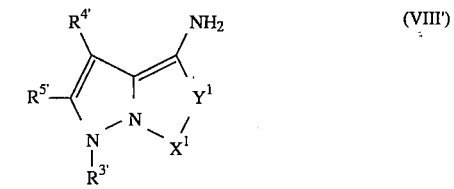

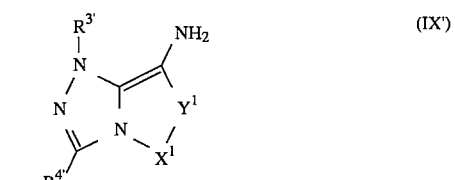

wherein X'—Y' is N=CR², R² is alkyl, alkenyl, alkoxy, alkylthio, aryl, aralkyl, wherein R² is unsubstituted or substituted by hydroxyl, dialkylphosphinyl, carboxyl, SO₃H, PO₃H₂, or a salt of one of the acid residues; or R² is alkoxycarbonyl or amino, which amino is unsubstituted or substituted by one or two alkyl radicals which alkyl are unsubstituted or substituted by one or more hydroxyl, carboxyl or alkoxycarbonyl radicals, whereby, when the amino is substituted by two alkyl radicals, the alkyls are linear or form a ring which, apart from the first nitrogen atom of the amino group, are uninterrupted or interrupted by oxygen, sulphur or a second nitrogen atom, or the amino is unsubstituted or substituted by one or two acyl radicals, alkoxy or aralkoxycarbonyl radicals, $H_2N-CO-$, alkyl, aralkyl, or arylcarbamoyl radicals; or $R^2$ is hydrogen, carboxyl, alkoxycarbonyl, carboxamido or halogen; $R^{3'}$ is alkyl or aralkyl and $R^{4'}$, $R^{5'}$, $R^{6'}$, and $R^{7'}$ are the same or different and are hydrogen, hydroxyl, alkyl, alkoxy, alkylthio, aralkyl, aryl, carboxyl, alkoxycarbonyl, carboxamido, cyano, amino which is unsubstituted or substituted by one or more alkyl wherein the alkyl is unsubstituted or substituted by at least one hydroxyl, carboxyl or alkoxycarbonyl, or halogen or two neighboring radicals form an alkylene which alkylene is unsubstituted or annellated with aryl as well as the corresponding tautomers and salts thereof with the proviso that (a) when $R^2$ of formula (II') is alkyl or aryl, $R^{4'}$, $R^{5'}$, $R^{6'}$, and $R^{7'}$ are not hydrogen, alkyl, alkoxy or halogen, and (b) when $R^{4'}$, $R^{5'}$, $R^{6'}$, of formula (III') are alkyl, alkoxy, alkylthio, hydroxyl, aryl, alkoxycarboxyl or halogen, $R^{2'}$ is not hydrogen or methyl.

2. A 3-amino pyrazolo derivative of claim 1 selected from the group of compounds of formula (VI'), (VII') and (VIII') as follows:

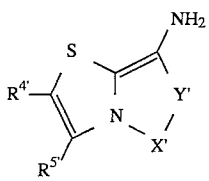

(VI')

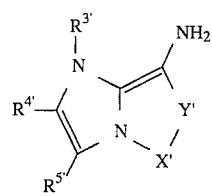

(VII')

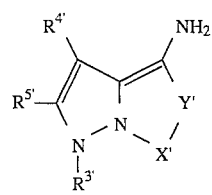

(VIII')

wherein X'—Y' and $R^{3'}$ have the same meanings as in claim 1 and $R^{4'}$ and $R^{5'}$ are the same or different and are hydrogen, hydroxyl, alkyl, alkoxy, alkylthio, aralkyl, aryl, carboxyl, alkoxycarbonyl, carboxamido, cyano, amino which is unsubstituted or substituted by one or two alkyl radicals which alkyls are unsubstituted or substituted by at least one hydroxyl, carboxyl or alkoxycarbonyl radicals, or halogen or two neighboring radicals form an alkylene radical which alkylene is unsubstituted or substituted or anellated with aryl, and tautomers and salts thereof.

3. A 3-amino pyrazolo derivative of claim 1 selected from the group of compounds of formula II'.

4. A 3-amino pyrazolo compound of claim 1 designated 3-amino-2-methylpyrazolo pyridine and the salts thereof.

* * * * *

UNITED STATES PATENT AND TRADEMARK OFFICE
CERTIFICATE OF CORRECTION

PATENT NO. : 5,457,200
DATED : October 10, 1995
INVENTOR(S) : Gerd Zimmermann et al., It is certified that error appears in the above-indentified patent and that said Letters Patent is hereby corrected as shown below:

| COLUMN | LINE | |
|---|---|---|
| 21 | 15 | Patent should read "2580" not "258C" |
| 30 | =45 | Example 31 - Patent should read " Chem Ber 2896/1956" not "Chem Ber", 89," |

Signed and Sealed this

Fourteenth Day of October, 1997

BRUCE LEHMAN

*Attest:*

*Attesting Officer*        *Commissioner of Patents and Trademarks*